(12) United States Patent
Soriano et al.

(10) Patent No.: US 11,708,609 B2
(45) Date of Patent: Jul. 25, 2023

(54) METHODS OF DIAGNOSING ALZHEIMER'S DISEASE AND RISK OF PROGRESSION TO ALZHEIMER'S DISEASE

(71) Applicant: Loma Linda University Health, Loma Linda, CA (US)

(72) Inventors: Salvador Soriano, Loma Linda, CA (US); Michael Castello, Loma Linda, CA (US)

(73) Assignee: Loma Linda University Health, Loma Linda, CA (US)

( * ) Notice: Subject to any disclaimer, the term of this patent is extended or adjusted under 35 U.S.C. 154(b) by 0 days.

(21) Appl. No.: 16/467,783

(22) PCT Filed: Dec. 8, 2017

(86) PCT No.: PCT/US2017/065367
§ 371 (c)(1),
(2) Date: Jun. 7, 2019

(87) PCT Pub. No.: WO2018/107059
PCT Pub. Date: Jun. 14, 2018

(65) Prior Publication Data
US 2019/0300960 A1 Oct. 3, 2019

Related U.S. Application Data

(60) Provisional application No. 62/432,091, filed on Dec. 9, 2016.

(51) Int. Cl.
*C12Q 1/6883* (2018.01)
*G01N 33/68* (2006.01)
*A61B 5/00* (2006.01)
*G01N 33/50* (2006.01)

(52) U.S. Cl.
CPC .............. *C12Q 1/6883* (2013.01); *A61B 5/00* (2013.01); *G01N 33/5023* (2013.01); *G01N 33/6896* (2013.01); *C12Q 2600/118* (2013.01); *C12Q 2600/136* (2013.01); *C12Q 2600/158* (2013.01); *G01N 2500/10* (2013.01); *G01N 2800/2821* (2013.01); *G01N 2800/50* (2013.01); *G01N 2800/52* (2013.01)

(58) Field of Classification Search
CPC ................................ C12Q 1/6883; A61B 5/00; G01N 2800/2821; G01N 2800/50
See application file for complete search history.

(56) References Cited

U.S. PATENT DOCUMENTS

| 9,410,204 B2 | 8/2016 | Sharp et al. |
| 2008/0248995 A1 | 10/2008 | Karnieli et al. |
| 2016/0040125 A1 | 2/2016 | Da Silva et al. |
| 2016/0320417 A1 | 11/2016 | Soriano et al. |

FOREIGN PATENT DOCUMENTS

EP 2 334 816 B1 11/2013

OTHER PUBLICATIONS

EPO Extended Search Report for EP Application No. 17878530.9, dated Dec. 3, 2020.
Pluta et al., "Alzheimer's Mechanisms in Ischemic Brain Degeneration", The Anatomical Record, (Feb. 18, 2009), vol. 292, pp. 1863-1881.
Manolopoulos et al., "Linking Alzheimer's disease to insulin resistance: the FoxO response to oxidative stress", Molecular Psychiatry, (Oct. 22, 2010), vol. 15, pp. 1046-1052.
Ghosal et al., "Alzheimer's disease-like pathological features in transgenic mice expressing the APP intracellular domain", Proceedings of the National Academy of Sciences of the USA, (Oct. 27, 2009), vol. 106, No. 43, pp. 18367-18372.
Borroni et al.: "Platelet Amyloid Precursor Protein Abnormalities in Mild Cognitive Impairment Predict Conversion to Dementia of Alzheimer Type: A 2-Year Follow-up Study", Archives of Neurology, vol. 60, No. 12,(Mar. 1, 2003), p. 1740.
Arisi et al.: "Supplementary Data Gene Expression Biomarkers in the Brain of a Mouse Model for Alzheimer's Disease: Mining of Microarray Data by Logic Classification and Feature Selection", Journal of Alzheimer's Disease, Jan. 1, 2011, pp. 1-72.
Arisi et al.: "Gene Expression Biomarkers in the Brain of a Mouse Model for Alzheimer's Disease: Mining of Microarray Data by Logic Classification and Feature Selection", Journal of Alzheimer's Disease, vol. 24, No. 4, May 30, 2011, pp. 721-738.
Ghosal et al., "Alzheimer's Disease-Like Pathological Features In Transgenic Mice Expressing The App Intracellular Domain", Proceedings of the National Academy of Sciences of the USA, vol. 106, No. 43, Oct. 27, 2009, pp. 18367-18372.
Gongol et al., "Cellular Hormetic Response to 27-Hydroxycholesterol Promotes Neuroprotection Through AICD Induction of MAST4 Abundance And Kinase Activity", Scientific Reports, vol. 7, No. 13898, Oct. 24, 2017, pp. 1-11.
Manolopoulos et al., "Linking Alzheimer's Disease to Insulin Resistance: The FoxO Response to Oxidative Stress", Molecular Psychiatry, vol. 15, No. 11, Oct. 22, 2010, pp. 1046-1052.
Pluta et al., "Alzheimer's Mechanisms in Ischemic Brain Degeneration", The Anatomical Record, vol. 292, Feb. 18, 2009, pp. 1863-1881.

(Continued)

*Primary Examiner* — Olga N Chernyshev
(74) *Attorney, Agent, or Firm* — Womble Bond Dickinson (US) LLP

(57) ABSTRACT

In one aspect, methods of diagnosing a subject as having Alzheimer's disease and prognosing a subject as being at risk of progressing to Alzheimer's disease are provided. In some embodiments, the method comprises determining one or more of the level of expression of rhotekin 2 (RTKN2), the level of expression of microtubule-associated Ser/Thr kinase 4 (MAST4), the level of binding of forkhead box O1 (FOXO1) to the RTKN2 promoter, and the level of binding of amyloid precursor protein (APP) to the MAST4 promoter in a sample from the subject.

8 Claims, 18 Drawing Sheets
Specification includes a Sequence Listing.

(56) References Cited

OTHER PUBLICATIONS

Shulman et al., "Functional Screening in *Drosophila* Identifies Alzheimer's Disease Susceptibility Genes And Implicates Tau-Mediated Mechanisms", Human Molecular Genetics, vol. 23, No. 4, Sep. 25, 2013, pp. 870-877.
PCT/US2017/065367, "International Search Report and Written Opinion", dated May 16, 2018, 14 pages.
International Application No. PCT/US2017/065367, International Preliminary Report on Patentability dated Jun. 20, 2019, 10 pages.
Examination Report for Australian Application No. 2017371071, dated Jun. 2, 2022.

FIG. 1E
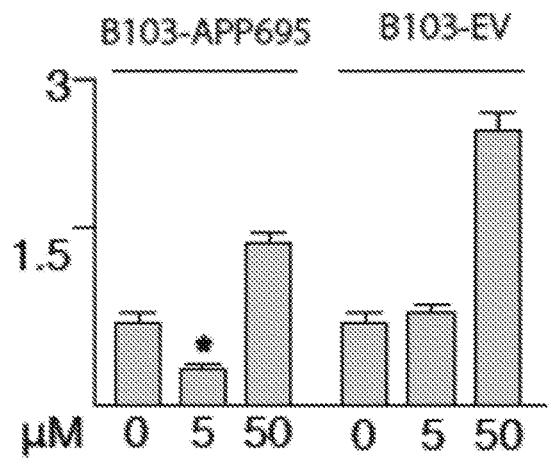
FIG. 1F
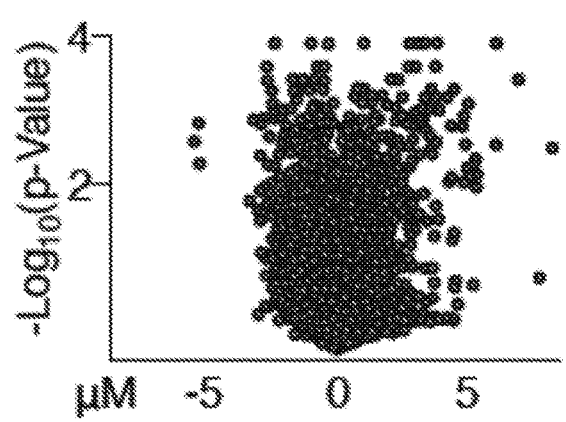
FIG. 1G
| Gene | FC APP-/-/WT | p-value |
|---|---|---|
| Zfp874a | 97.8144 | 3e-04 |
| Psmg2 | 11.6041 | 2e-04 |
| Siah3 | 7.6241 | 1e-04 |
| Eps8l1 | 6.2189 | 1e-04 |
| Zfp146 | 5.9983 | 2e-04 |
| Gria2 | 4.3308 | 3e-04 |
| BC049715 | -5.7198 | 2e-04 |
| Mast4 | -5.8718 | 3e-04 |

METHODS OF DIAGNOSING ALZHEIMER'S DISEASE AND RISK OF PROGRESSION TO ALZHEIMER'S DISEASE

CROSS-REFERENCE TO RELATED APPLICATIONS

This application claims priority to U.S. Provisional Patent Application No. 62/432,091, filed Dec. 9, 2016, the entire contents of which are incorporated by reference herein.

SEQUENCE LISTING

The instant application contains a Sequence Listing which has been submitted electronically in ASCII format and is hereby incorporated by reference in its entirety. Said ASCII copy, created on Apr. 26, 2021, is named 105781_0111_1_16-018_SL.txt and is 10,498 bytes in size.

BACKGROUND OF THE INVENTION

Alzheimer's disease is a progressive brain disorder characterized by memory loss, impaired cognition, and impaired reasoning or judgment. Alzheimer's disease is the most common form of dementia, and it is estimated that about 5 million Americans may have the disease.

Despite years of research, the mechanisms that lead to Alzheimer's disease pathology remain unknown. The amyloid cascade hypothesis proposes that Alzheimer's disease is caused by the accumulation, oligomerization, and aggregation of amyloid-beta peptide (Aβ) in extracellular deposits. Aβ is proteolytically derived from the Amyloid Precursor Protein (APP), and therefore, therapeutic approaches to the treatment of Alzheimer's disease have focused on preventing the accumulation of Aβ in the brain in order to ameliorate or halt the disease. However, numerous drugs aimed at reducing the burden of Aβ in the brain have failed to treat Alzheimer's disease. See, e.g., Castello et al., *BMC Neurology*, 2014, 14:169. Moreover, a significant portion of the cognitively healthy population show accumulation of Aβ in the brain (see, e.g., Aizenstein et al., Arch Neurol, 2008, 65:1509-1517), indicating that Aβ is neither necessary nor sufficient to initiate the disease.

Accordingly, there remains a need for methods of diagnosing Alzheimer's disease and for compositions and methods for treating Alzheimer's disease.

BRIEF SUMMARY OF THE INVENTION

In one aspect, methods of prognosing a subject at risk of progressing to Alzheimer's disease are provided. In some embodiments, the method comprises:

detecting one or more of (i) a decreased level of expression of RTNK2 mRNA or protein, (ii) a decreased level of MAST4 mRNA or protein, (iii) an increased level of binding of FOXO1 to the RTKN2 promoter, or (iv) an increased level of binding of APP or a fragment thereof comprising the APP intracellular domain to the MAST4 promoter in a sample from the subject relative to a reference value;

thereby prognosing the subject as being at risk of progressing to Alzheimer's disease.

In some embodiments, the subject has Mild Cognitive Impairment.

In some embodiments, the method comprises detecting a decreased level of expression of RTNK2 mRNA or protein in the sample from the subject (e.g., decreased by at least 10%, at least 20%, at least 30%, at least 40%, at least 50%, at least 60%, at least 70%, at least 80%, at least 90% or more as compared to the reference value). In some embodiments, the method comprises detecting a decreased level of MAST4 mRNA or protein in the sample from the subject (e.g., decreased by at least 10%, at least 20%, at least 30%, at least 40%, at least 50%, at least 60%, at least 70%, at least 80%, at least 90% or more as compared to the reference value). In some embodiments, the method comprises detecting an increased level of binding of FOXO1 to the RTKN2 promoter in the sample from the subject (e.g., increased by at least 10%, at least 20%, at least 30%, at least 40%, at least 50%, at least 60%, at least 70%, at least 80%, at least 90% or more as compared to the reference value). In some embodiments, the method comprises detecting an increased level of binding of APP or a fragment thereof comprising the APP intracellular domain to the MAST4 promoter in the sample from the subject (e.g., increased by at least 10%, at least 20%, at least 30%, at least 40%, at least 50%, at least 60%, at least 70%, at least 80%, at least 90% or more as compared to the reference value). In some embodiments, the method comprises detecting a decreased level of expression of RTNK2 mRNA or protein and at least one or more of (ii), (iii), and (iv) in a sample from the subject. In some embodiments, the method comprises detecting two or more of (i), (ii), (iii), and (iv) in a sample from the subject. In some embodiments, the method comprises detecting each of (i), (ii), (iii), and (iv) in a sample from the subject.

In some embodiments, the method of prognosing a subject as being at risk of progressing to Alzheimer's disease further comprises detecting decreased phosphorylation of FOXO1 in the sample from the subject, as compared to a reference value (e.g., decreased by at least 10%, at least 20%, at least 30%, at least 40%, at least 50%, at least 60%, at least 70%, at least 80%, at least 90% or more as compared to the reference value). In some embodiments, the method of prognosing a subject as being at risk of progressing to Alzheimer's disease further comprises detecting an increased level of filipin in the sample from the subject, as compared to a reference value (e.g., increased by at least 10%, at least 20%, at least 30%, at least 40%, at least 50%, at least 60%, at least 70%, at least 80%, at least 90% or more as compared to the reference value).

In some embodiments, for a subject who is identified as being at risk of progressing to Alzheimer's disease, the method further comprises administering one or more therapeutic interventions to the subject. In some embodiments, the therapeutic intervention comprises a dietary modification. In some embodiments, the therapeutic intervention comprises administering a lipid-lowering or cholesterol-lowering medication. In some embodiments, the therapeutic intervention comprises administering a compound that increases RTKN2 expression in the subject.

In another aspect, methods for diagnosing a subject as having Alzheimer's disease are provided. In some embodiments, the method comprises:

measuring in a sample from the subject one or more of (i) the level of expression of a rhotekin 2 (RTKN2) polynucleotide or protein, (ii) the level of expression of microtubule-associated Ser/Thr kinase 4 (MAST4) polynucleotide or protein, (iii) the level of binding of forkhead box O1 (FOXO1) to the RTKN2 promoter; and (iv) the level of binding of amyloid precursor protein (APP) or a fragment thereof comprising the APP intracellular domain to the MAST4 promoter; and; comparing one or more of (I) the level of expression of the RTKN2 polynucleotide or protein, (ii) the level of expression of the MAST4 polynucleotide or protein, (iii) the level of binding of FOXO1 to the RTKN2 promoter, and (iv) the level of binding of APP or the fragment thereof to the MAST4 promoter in the sample from the subject to a reference value;

wherein one or more of (i) decreased expression of RTKN2, (ii) decreased expression of MAST4, (iii) increased binding of FOXO1 to the RTKN2 promoter, and (iv) decreased binding of APP or the fragment thereof to the MAST4 promoter in the sample from the subject, as compared to the reference value, identifies the subject as having Alzheimer's disease.

In some embodiments, the method comprises:
measuring in a sample from the subject (i) the level of expression of a RTKN2 polynucleotide or protein, and (ii) the level of expression of a MAST4 polynucleotide or protein; and comparing (i) the level of expression of the RTKN2 polynucleotide or protein, and (ii) the level of expression of the MAST4 polynucleotide or protein in the sample from the subject to a reference value;

wherein (i) decreased expression of RTKN2, and (ii) decreased expression of MAST4, as compared to the reference value, identifies the subject as having Alzheimer's disease.

In some embodiments, the method comprises:
measuring in a sample from the subject (i) the level of expression of a RTKN2 polynucleotide or protein, (ii) the level of expression of a MAST4 polynucleotide or protein, (iii) the level of binding of FOXO1 to the RTKN2 promoter; and (iv) the level of binding of APP, or a fragment thereof comprising the APP intracellular domain, to the MAST4 promoter; and comparing (i) the level of expression of RTKN2 polynucleotide or protein, (ii) the level of expression of MAST4 polynucleotide or protein, (iii) the level of binding of FOXO1 to the RTKN2 promoter, and (iv) the level of binding of APP or the fragment thereof to the MAST4 promoter in the sample from the subject to a reference value;

wherein (i) decreased expression of RTKN2, (ii) decreased expression of MAST4, (iii) increased binding of FOXO1 to the RTKN2 promoter, and (iv) decreased binding of APP or the fragment thereof to the MAST4 promoter in the sample from the subject, as compared to the reference value, identifies the subject as having Alzheimer's disease.

In some embodiments, the method comprises measuring the level of expression of RTKN2 and/or MAST4 mRNA by quantitative PCR. In some embodiments, the method comprises measuring the level of binding of FOXO1 binding to the RTKN2 promoter and/or the level of binding of APP to the MAST4 promoter by chromatin IP coupled to PCR.

In some embodiments, the sample comprises blood, serum, plasma, or cerebrospinal fluid.

In some embodiments, the method further comprises:
measuring the level of phosphorylation of FOXO1 in the sample from the subject; and
comparing the level of phosphorylation of FOXO1 in the sample from the subject to a reference value;
wherein decreased phosphorylation of FOXO1 in the sample from the subject, as compared to the reference value, identifies the subject as having Alzheimer's disease.

In some embodiments, the method further comprises:
measuring the level of filipin in the sample from the subject; and comparing the level of filipin in the sample from the subject to a reference value;
wherein an increased level of filipin in the sample from the subject, as compared to the reference value, identifies the subject as having Alzheimer's disease.

In some embodiments, subsequent to identifying the subject as having Alzheimer's disease, the method further comprises administering one or more therapeutic interventions to the subject. In some embodiments, the therapeutic intervention comprises a dietary modification. In some embodiments, the therapeutic intervention comprises administering a lipid-lowering or cholesterol-lowering medication. In some embodiments, the therapeutic intervention comprises administering a compound that increases RTKN2 expression in the subject.

In another aspect, methods of detection are provided. In some embodiments, the method comprises:
obtaining a sample from a subject (e.g., a subject at risk of having Alzheimer's disease or a subject suspected of having Alzheimer's disease); and
measuring in a sample from the subject one or more of (i) the level of expression of a rhotekin 2 (RTKN2) polynucleotide or protein, (ii) the level of expression of microtubule-associated Ser/Thr kinase 4 (MAST4) polynucleotide or protein, (iii) the level of binding of forkhead box O1 (FOXO1) to the RTKN2 promoter; and (iv) the level of binding of amyloid precursor protein (APP) or a fragment thereof comprising the APP intracellular domain (AICD) to the MAST4 promoter.

In some embodiments, the method comprises measuring the level of expression of RTKN2 and/or MAST4 mRNA by quantitative PCR. In some embodiments, the method comprises measuring the level of expression of RTKN2 and/or MAST4 mRNA by quantitative PCR using one or more primers disclosed in Table 1. In some embodiments, the method comprises measuring the level of binding of FOXO1 binding to the RTKN2 promoter and/or the level of binding of APP to the MAST4 promoter by chromatin IP coupled to PCR In some embodiments, the method comprises measuring the level of binding of FOXO1 binding to the RTKN2 promoter and/or the level of binding of APP to the MAST4 promoter by chromatin IP coupled to PCR using one or more primers disclosed in Table 1.

In some embodiments, the sample comprises blood, serum, plasma, or cerebrospinal fluid.

In another aspect, methods of treating a subject by delaying or reversing the progression of Alzheimer's disease are provided. In some embodiments, the method comprises:
measuring in a sample from the subject one or more of (i) the level of expression of rhotekin 2 (RTKN2) mRNA or protein, (ii) the level of expression of microtubule-associated Ser/Thr kinase 4 (MAST4) mRNA or protein, (iii) the level of binding of forkhead box O1 (FOXO1) to the RTKN2 promoter; and (iv) the level of binding of amyloid precursor protein (APP) or a fragment thereof comprising the APP intracellular domain to the MAST4 promoter;
determining that the sample from the subject has one or more of (i) a decreased level of expression of RTKN2 mRNA or protein, (ii) a decreased level of expression of MAST4 mRNA or protein, (iii) an increased level of binding of FOXO1 to the RTKN2 promoter, and (iv) a decreased level of binding of APP, or the fragment thereof, to the MAST4 promoter, as compared to a reference value; and administering a therapeutic intervention to the subject; thereby treating the subject.

In some embodiments, the method comprises:

measuring in a sample from the subject (i) the level of expression of a RTKN2 polynucleotide or protein, and (ii) the level of expression of a MAST4 polynucleotide or protein; and determining that the sample from the subject has (i) decreased expression of RTKN2, and (ii) decreased expression of MAST4, as compared to the reference value.

In some embodiments, the method comprises:

measuring in a sample from the subject (i) the level of expression of a RTKN2 polynucleotide or protein, (ii) the level of expression of a MAST4 polynucleotide or protein, (iii) the level of binding of FOXO1 to the RTKN2 promoter; and (iv) the level of binding of APP, or a fragment thereof comprising the APP intracellular domain, to the MAST4 promoter; and determining that the sample from the subject has (i) decreased expression of RTKN2, (ii) decreased expression of MAST4, (iii) increased binding of FOXO1 to the RTKN2 promoter, and (iv) decreased binding of APP or the fragment thereof to the MAST4 promoter in the sample from the subject, as compared to the reference value.

In some embodiments, the therapeutic intervention comprises a dietary modification. In some embodiments, the therapeutic intervention comprises administering a lipid-lowering or cholesterol-lowering medication. In some embodiments, the therapeutic intervention comprises administering a compound that increases RTKN2 expression in the subject.

In yet another aspect, methods of identifying a compound for delaying the progression of Alzheimer's disease are provided. In some embodiments, the method comprises:
(a) contacting one or more compounds to a cell or a population of cells;
(b) determining whether the one or more compounds increases the level of expression of rhotekin 2 (RTKN2) in the cell or population of cells, relative to a reference value; and
(c) selecting for the one or more compounds that increases the level of expression of RTKN2 in the cell or population of cells.

In some embodiments, the method further comprises determining whether the one or more compounds increases the level of expression of microtubule-associated Ser/Thr kinase 4 (MAST4) in the cell or population of cells, relative to the reference value, and selecting for the one or more compounds that increases the level of expression of MAST4 in the cell or population of cells.

In some embodiments, the level of expression is measured by quantitative PCR.

In some embodiments, the method further comprises subjecting the cell or population of cells to one or more stress stimuli and selecting the one or more compounds that increase cell survival in the presence of the one or more stress stimuli, relative to a reference value. In some embodiments, the stress stimulus is oxysterol or palmitic acid.

In some embodiments, the cell is a human cell. In some embodiments, the cell is from a subject having Alzheimer's disease.

In some embodiments, the method further comprises chemically synthesizing a structurally related analog of the one or more selected-for compounds.

In another aspect, methods of delaying the progression of Alzheimer's disease in a subject, or methods of delaying the progression into Alzheimer's disease in a subject having mild cognitive impairment, are provided. In some embodiments, the method comprises administering to the subject a compound identified by a method as described herein or a chemically synthesized analog thereof.

BRIEF DESCRIPTION OF THE DRAWINGS

FIG. 1A-FIG. 1I. APP elicits a hormetic response against 27OHC cytotoxicity. (A, B) Neuron-differentiated SH-SY5Y cells were treated with the indicated concentrations of 27OHC (A) or 24OHC (B) for 18 hours and LDH release determined. 27OHC elicited a biphasic response in which concentrations below 10 μM lead to decreased LDH compared to baseline (solvent alone) and higher concentrations lead to dose-dependent cytotoxicity. No LDH changes are measurable in response to different doses of 24OHC. (C) B103 cells, which lack APP, were stably transfected with the 695 amino acid isoform of APP (B103-APP$_{695}$) or with empty host vector pcDNA3.1 (B103-EV), and treated with the indicated concentrations of 27OHC for 18 hours and LDH release determined. Cytotoxicity is dose-dependent in the absence of APP but follows a biphasic pattern comparable to that seen in (A) in B103-APP$_{695}$ cells. (D, E) B103-EV and B103-APP$_{695}$ cells were treated with 27OHC as indicated and membrane integrity measured and quantitated with a LIVE/DEAD assay. (D) Representative micrograph of cells lacking (B103-EV; upper panel) or expressing APP (B103-APP$_{695}$; lower panel) showing green-stained live cells and red-stained dead cells. (E) Quantitation of cell viability using LIVE/DEAD assay, shown as the percentage of shown in (D), confirming an APP-dependent biphasic response to 27OHC. (F). Volcano plot showing global transcriptional changes in mouse brain cortex of App$^{wt}$ and App$^{ko}$ genotypes. Each circle represents one gene. (G) representation of most significantly differentially expressed genes between App$^{wt}$ and App$^{ko}$ cortices. (H) Schematic representation of strategy to identify genes involved in the APP-dependent hormetic response to 27OHC. FIG. 1H discloses SEQ ID NO: 40. (I) Illustrated hypothesis for the effects of 5 or 50 μM 27OHC on APP, MAST4, FOXO1, and RTKN2. At cytoprotective doses, 27OHC elicits AICD-driven modulation of MAST4, which in turn could lead to FOXO1 transcriptional regulation of RTKN2 to optimize cell survival.

FIG. 3B discloses SEQ ID NOS 41, 41 and 41. (C-F) ChIP assays for the binding of FOXO1 to the RTKN2 promoter in neuron-differentiated SH-SY5Y cells transfected with control (SCR), APP or MAST4 siRNA (C), or with FOXO1 wild-type (FOXO1-WT) or DNA-binding deficient (FOXO1-DBD) mutant forms (D); in B103 cells transfected with $APP_{695}$ or $APP_{G700A}$ (E), and in rat cortical neurons (F). (G-J) RTKN2 mRNA in neuron-differentiated SH-SY5Y cells transfected with control (SCR), APP, MAST4 and FOXO1 siRNA (G), or with FOXO1 wild-type (FOXO1-WT) or DNA-binding deficient (FOXO1-DBD) mutant forms (H); in B103 cells transfected with $APP_{695}$ or $APP_{G700A}$ (I), and in rat cortical neurons (J).

DETAILED DESCRIPTION OF THE INVENTION

I. Introduction

Figure 1A:
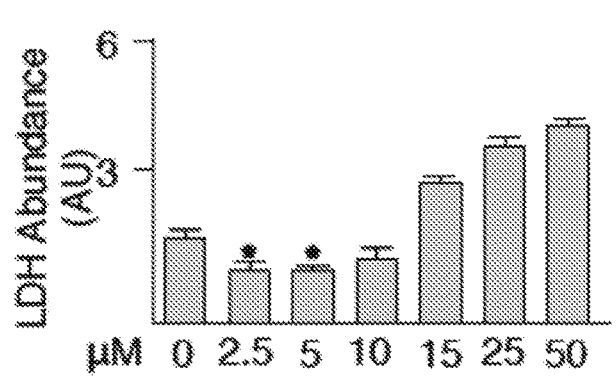

The amyloid precursor protein (APP) is a precursor molecule that, when proteolytically cleaved, generates amyloid-beta peptide (Aβ). The biological function of APP in the brain remains unresolved, a shortcoming that hinders the understanding of the etiology of late-onset Alzheimer's disease. Most research into the causes of and treatments for Alzheimer's disease are driven by the premises of the amyloid cascade hypothesis, which proposes that Alzheimer's disease is caused by the accumulation, oligomerization, and aggregation of amyloid-beta peptide (Aβ) in extracellular deposits. However, the amyloid cascade hypothesis, which views the role of APP solely as a precursor of Aβ within a primary pathogenic cascade, does not fit the available evidence. See, e.g., Castello et al., *BMC Neural*, 2014, 14:169; Castellani et al, *J Alzheimers Dis*, 2009, 18:447-452; and Herrup, *Nat Neurosci*, 20:15, 18:794-799.

An alternative hypothesis has been proposed for how Alzheimer's disease begins and develops. This hypothesis, called the adaptive response hypothesis, postulates that Aβ is a protective molecule that is regulated in response to chronic stress in the brain, such as oxidative stress, metabolism dysregulation (e.g., cholesterol homeostasis and insulin resistance), genetic factors, and inflammation response. In this hypothesis, the presence of Aβ is evidence of an ongoing stress process, rather than a marker of disease initiation. See, e.g., Castello et al., *BMC Neural*, 2014, 14:169; and Castello et al., *Ageing Research Reviews*, 2014, 13:10-12.

As described herein, it has been found that APP regulates an adaptive response to an early marker of cholesterol dysregulation in the Alzheimer's disease brain and protects the brain from cholesterol oxidation. Without being bound to a particular theory, it is believed that the genes RTKN2, MAST4, FOXO1, and APP act as "brain protectors" that function in a hormetic adaptive response to stress stimuli. In patients with Alzheimer's disease, the expression and/or activity of these genes are severely deficient. Thus, in one aspect, these genes represent biomarkers for diagnosing a subject as having Alzheimer's disease. The identification of these biomarkers that can be assayed in blood samples from a subject is valuable at least because it provides a minimally invasive method for diagnosing Alzheimer's disease, and because it is possible to detect molecular changes that develop at an early stage of the disease. Furthermore, as detailed below, therapeutic interventions can be designed that increase the expression or activity of these "brain protective" genes, thereby delaying or even reversing the progression of Alzheimer's disease.

II. Definitions

The terminology used herein is for the purpose of describing particular embodiments only, and is not intended to be limiting, because the scope of the present invention will be limited only by the appended claims. Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings unless a contrary intention is apparent. In some cases, terms with commonly understood meanings are defined herein for clarity and/or for ready reference, and the inclusion of such definitions herein should not be construed as representing a substantial difference over the definition of the term as generally understood in the art.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about."

The singular forms "a," "an," and "the" include plural referents unless the context clearly dictates otherwise. Thus, for example, reference to "a compound" includes a plurality of compounds.

The term "comprising" is intended to mean that the compounds, compositions and methods include the recited elements, but not excluding others. "Consisting essentially of" when used to define compounds, compositions and methods, shall mean excluding other elements that would materially affect the basic and novel characteristics of the claimed invention. "Consisting of" shall mean excluding any element, step, or ingredient not specified in the claim. Embodiments defined by each of these transition terms are within the scope of this invention.

As used herein, "Alzheimer's disease" refers to a disease characterized by progressive cognitive impairment. The symptoms of Alzheimer's disease typically worsen over time as the disease progresses, with the disease typically progressing through three stages: "mild" (an early-stage form of Alzheimer's disease), "moderate" (a middle-stage form), and "severe" (a late-stage form). In mild Alzheimer's disease, symptoms may include, for example, memory loss, losing or misplacing objects, trouble remembering names or recalling words, increased difficulty with planning or organizing, taking longer to complete normal daily tasks, and repeating questions. In moderate Alzheimer's disease, which is typically the longest stage of the disease for many patients, damage occurs in areas of the brain that control language, reasoning, sensory processing, and conscious thought. In this stage, symptoms may include, for example, forgetfulness of events or of one's one personal history, problems recognizing family and friends, inability to learn new information, difficulty carrying out multi-step tasks, impulsive behavior, changes in sleep patterns, hallucinations, delusions, and paranoia. In severe Alzheimer's disease, memory and cognitive skills continue to worsen, patients typically lose the ability to respond to their environment, carry on a conversation, and/or control movement, and patients require a high level of assistance with daily activities and personal care.

In some embodiments, a patient has "late onset" Alzheimer's disease, which refers to a form of Alzheimer's disease in which the patient exhibits clinical symptoms of the disease after about age 65. In some embodiments, a patient has "early onset" Alzheimer's disease, which refers to a form of Alzheimer's disease in which a patient exhibits the onset of clinical symptoms of the disease prior to the age of 65. In some embodiments, patients having early onset Alzheimer's disease exhibit the onset of clinical symptoms of the disease in their 30s, 40s, or 50s. In some embodiments, the early onset Alzheimer's disease is early onset familial Alzheimer's disease (FAD), which is a hereditary form of Alzheimer's disease caused by autosomal dominant mutations that affect APP processing.

As used herein, "Mild Cognitive Impairment" refers to a disorder that is characterized by a decline in cognitive abilities (such as memory and thinking skills) that is greater than expected for an individual's age and education level but that does not interfere notably with activities of daily life. See, Gauthier et al., *Lancet*, 2006, 367-1262-1270.

As used herein, "RTKN2" refers to "rhotekin 2." The protein encoded by the RTKN2 gene is a Rho-GTPase effector that is characterized in part by the presence of a Rho binding domain and a pleckstrin homology domain. See, Collier et al., *Biochem Biophys Res Commun*, 2004, 324: 1360-1360. Human RTKN2 gene and protein sequences, including all currently known splice and isoform variants, are set forth in, e.g., NCBI GenBank Accession Nos. NM_145307.3, NM_001282941.1, XR_001747053.1, XR_945618.2, XM_017015844.1, XM_017015842.1, XM_011539456.2, AAI42726.1, AAI41822.1, AAH25765.1, NP_001269870.1, NP_660350.2, XP_016871333.1, XP_016871332.1, XP_016871331.1, XP_011537762.1, XP_011537759.1, XP_011537758.1, and AAN71738.1. In some embodiments, a RTKN2 gene or protein to be detected according to the methods described herein is a variant having at least 70%, at least 75% at least 80%, at least 85%, at least 90%, at least 91%, at least 92%, at least 93%, at least 94%, at least 95%, at least 96%, at least 97%, at least 98%, or at least 99% identity to a naturally occurring RTKN2 gene or protein set forth in any of NCBI GenBank Accession Nos. NM_145307.3, NM_001282941.1, XR_001747053.1, XR_945618.2, XM_017015844.1, XM_017015842.1, XM_011539456.2, AAI42726.1, AAI41822.1, AAH25765.1, NP_001269870.1, NP_660350.2, XP_016871333.1, XP_016871332.1, XP_016871331.1, XP_011537762.1, XP_011537759.1, XP_011537758.1, or AAN71738.1.

As used herein, "MAST4" refers to "microtubule-associated Ser/Thr kinase 4." The protein encoded by the MAST4 gene is a kinase characterized by the presence of a serine/threonine kinase domain and a PDZ domain. See, Garland et al., *Brain Res*, 2008, 1195_12-19. Human MAST4 gene and protein sequences, including all currently known splice and isoform variants, are set forth in, e.g., NCBI GenBank Accession Nos. NM_001297651.1, NG_034036.1, NM_001290227.1, NM_001290226.1, NM_001164664.1, NM_015183.2, NM_198828.2, XM_017009453.1, XM_017009452.1, XM_017009451.1, XM_006714610.2, XM_011543386.2, XM_011543385.2, XM_017009450.1, XM_011543384.2, XM_006714606.3, XM_017009449.1, XM_017009448.1, XM_011543382.2, XM_017009447.1, NP_001284580.1, NP_001277156.1, NP_001277155.1, NP_001158136.1, NP_055998.1, NP_942123.1, XP_016864942.1, XP_016864941.1, XP_016864940.1, XP_016864939.1, XP_016864938.1, XP_016864937.1, XP_016864936.1, XP_011541688.1, XP_011541687.1, XP_011541686.1, XP_011541684.1, XP_006714673.1, and XP_006714669.3 or in UniProtKB Database Accession No. O15021.3. In some embodiments, a MAST4 gene or protein to be detected according to the methods described herein is a variant having at least 70%, at least 75% at least 80%, at least 85%, at least 90%, at least 91%, at least 92%, at least 93%, at least 94%, at least 95%, at least 96%, at least 97%, at least 98%, or at least 99% identity to a naturally occurring MAST4 gene or protein set forth in any of NCBI GenBank Accession Nos. NM_001297651.1, NG_034036.1, NM_001290227.1, NM_001290226.1, NM_001164664.1, NM_015183.2, NM_198828.2, XM_017009453.1, XM_017009452.1, XM_017009451.1, XM_006714610.2, XM_011543386.2, XM_011543385.2, XM_017009450.1, XM_011543384.2, XM_006714606.3, XM_017009449.1, XM_017009448.1, XM_011543382.2, XM_017009447.1, NP_001284580.1, NP_001277156.1, NP_001277155.1, NP_001158136.1, NP_055998.1, NP_942123.1, XP_016864942.1, XP_016864941.1, XP_016864940.1, XP_016864939.1, XP_016864938.1, XP_016864937.1, XP_016864936.1, XP_011541688.1, XP_011541687.1, XP_011541686.1, XP_011541684.1, XP_006714673.1, or XP_006714669.1 or in UniProtKB Database Accession No. O15021.3.

As used herein, "FOXO1" refers to "forkhead box O1." The protein encoded by the FOXO1 gene is a transcription factor that is characterized by the presence of a forkhead domain and that regulates a diverse set of subcellular systems in response to cellular stress. See, Martins et al., *Aging Cell*, 2016, 15:196-207. Human FOXO1 gene and protein sequences, including all splice and isoform variants, are set forth in, e.g., NCBI GenBank Accession Nos. NG_023244.1, NM_002015.3, NC_000013.11, NC_018924.2, XM_011535010.2, XM_011535008.2, BC070065.1, BCO21981.2, HF583666.1, NP_002006.2, XP_011533312.1, XP_011533310.1, AAH70065.3, AAH21981.1, and CCQ43163.1. In some embodiments, the FOXO1 gene or protein is a variant (e.g., polymorphic variant, splice variant, or truncated protein) having at least 70%, at least 75% at least 80%, at least 85%, at least 90%, at least 91%, at least 92%, at least 93%, at least 94%, at least 95%, at least 96%, at least 97%, at least 98%, or at least 99% identity to a naturally occurring FOXO1 gene or protein set forth in any of NCBI GenBank Accession Nos. NG_023244.1, NM_002015.3, NC_000013.11, NC_018924.2, XM_011535010.2, XM_011535008.2, BC070065.1, BCO21981.2, HF583666.1, NP_002006.2, XP_011533312.1, XP_011533310.1, AAH70065.3, AAH21981.1, or CCQ43163.1.

As used herein, "APP" refers to "amyloid precursor protein." The protein encoded by the APP gene is a type I membrane protein having an E1 domain and E2 domain. Cleavage of the APP protein produces an amyloid beta (Aβ) fragment and the APP intracellular domain (AICD). See, Zheng et al., *Mol Neurodegener*, 2006, 1:5 (doi: 10.1186/1750-13264-5). Human APP gene and protein sequences, including all splice and isoform variants, are set forth in, e.g., NCBI GenBank Accession Nos. AH005295.2, NM_000484.3, NM_001136131.2, NM_001136016.3, NM_001204303.1, NM_001204301.1, NM_001204302.1, NM_201414.2, NM_201413.2, NM_001136129.2, NM_001136130.2, BC065529.1, BC004369.1, HF583435.1, X06989.1, D87675.1, AAB59502.1, AAB59501.1, NP_000475.1, NP_001191232.1, NP_001191230.1, NP_001191231.1, NP_001129603.1, NP_001129602.1, NP_001129601.1, NP_001129488.1, NP_958817.1, NP_958816.1, EAX09966.1, EAX09965.1, EAX09964.1, EAX09963.1, EAX09962.1, EAX09961.1, EAX09960.1, EAX09959.1, EAX09958.1, EAX09957.1, AAH65529.1, AAW82435.1, CAA30050.1, and BAA22264.1. In some embodiments, the APP gene or protein is a variant (e.g., polymorphic variant, splice variant, or truncated protein) having at least 70%, at least 75% at least 80%, at least 85%, at least 90%, at least 91%, at least 92%, at least 93%, at least 94%, at least 95%, at least 96%, at least 97%, at least 98%, or at least 99% identity to a naturally occurring APP gene or protein set forth in any of NCBI GenBank Accession Nos. AH005295.2, NM_000484.3, NM_001136131.2, NM_001136016.3, NM_001204303.1, NM_001204301.1, NM_001204302.1, NM_201414.2, NM_201413.2, NM_001136129.2, NM_001136130.2, BC065529.1, BC004369.1, HF583435.1, X06989.1, D87675.1, AAB59502.1, AAB59501.1, NP_000475.1, NP_001191232.1, NP_001191230.1, NP_001191231.1, NP_001129603.1, NP_001129602.1, NP_001129601.1, NP_001129488.1, NP_958817.1, NP_958816.1, EAX09966.1, EAX09965.1, EAX09964.1, EAX09963.1, EAX09962.1, EAX09961.1, EAX09960.1, EAX09959.1, EAX09958.1, EAX09957.1, AAH65529.1, AMA/82435.1, CAA30050.1, or BAA22264.1. In some embodiments, the APP protein is a fragment comprising the APP intracellular domain, which is termed gamma-secretase C-terminal fragment 59, spanning inclusively amino acids 712-770 (having the sequence IATVIVITLMLKKKQYTSIHHGVVEVDAAVTPEERHLSKMQQNGYENPTYKFFEQMQN), or gamma-secretase C-terminal fragment 57, spanning inclusively amino acids 7:14-770 (having the sequences TVIVITLVMLKKKQYTSIHHGVVEVDAAVTPEERHLSKMQQNGYENPTYKFFEQMQN), or gamma-secretase C-terminal fragment 50, spanning inclusively amino acids 721-770 (having the sequence VMLKKKQYTSIHHGVVEVDAAVTPEERHLSKMQQNGYENPTYKFFEQMQN) (all numbers corresponding to the APP isoform containing 770 amino acids).

The terms "identical" or "percent identity," in the context of two or more polynucleotide or polypeptide sequences, refer to two or more sequences that are the same or have a specified percentage of amino acid residues or nucleotides that are the same (e.g., about 60% identity, preferably 65%, 70%, 75%, 80%, 85%, 90%, 91%, 92%, 93%, 94%, 95%, 96%, 97%, 98%, 99%, or higher identity) over a specified region. Methods for comparing polynucleotide or polypeptide sequences and determining percent identity are described in the art. See, e.g., Roberts et al., *BMC Bioinformatics*, 7:382, 2006, incorporated by reference herein.

The terms "nucleic acid" and "polynucleotide" are used interchangeably herein and refer to deoxyribonucleotides or ribonucleotides and polymers thereof in either single- or double-stranded form, and complements thereof. In some embodiments, the polynucleotide is DNA (e.g., genomic DNA or cDNA). In some embodiments, the polynucleotide is RNA (e.g., mRNA). Unless otherwise indicated, a particular nucleic acid sequence also implicitly encompasses conservatively modified variants thereof (e.g., degenerate codon substitutions), polymorphic variants (e.g., SNPs), splice variants, and nucleic acid sequences encoding truncated forms of proteins, complementary sequences, as well as the sequence explicitly indicated.

The terms "protein" and "polypeptide" are used interchangeably herein and refer to a polymer of amino acid residues. As used herein, the terms encompass amino acid chains of any length, including full-length proteins and truncated proteins.

As used herein, "filipin" refers to a polyene macrolide compound that was originally isolated from *Streptomyces filipinensis* and that exhibits intrinsic fluorescence. Filipin is known in the art as a diagnostic tool for diseases of lipid dysregulation, See, e.g., Dist; et al., *The Journal of Pathology*, 2003, 200:104-111. The structure and fluorescent properties of filipin are described, e.g., in Castanho et al., *Eur. J. Biochem.*, 1992, 207:125-134; and Xu et al., *J. Biol. Chem.*, 2010, 285:16844-16853.

As used herein, the term "compound" refers to any molecule, either naturally occurring or synthetic, e.g., peptide, protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, peptidamimetic, lipid, fatty acid, siRNA, polynucleotide, oligonucleotide, etc.

As used herein, an "analog" refers to a compound that is a structural derivative of a parent compound, in which one or more atoms or functional groups is different from the parent compound. In some embodiments, an analog has comparable or superior stability, solubility, efficacy, half-life, and the like as compared to the parent compound.

As used herein, a "biological sample" refers to a bodily tissue or fluid obtained from a human or non-human mammalian subject. In some embodiments, a sample comprises blood, blood fractions, or blood products (e.g., serum, plasma, platelets, red blood cells, peripheral blood mononuclear cells, and the like), sputum or saliva, stool, urine, other biological fluids lymph, saliva, prostatic fluid, gastric fluid, intestinal fluid, renal fluid, lung fluid, cerebrospinal fluid, and the like), tissue (e.g., kidney, lung, liver, heart, brain, nervous tissue, thyroid, eye, skeletal muscle, cartilage, or bone tissue), or cultured cells (e.g., primary cultures, explants, transformed cells, or stem cells). In some embodiments, a biological sample comprises blood. In some embodiments, a biological sample comprises cerebrospinal fluid (CSF).

A "subject" is a mammal, in some embodiments, a human. Mammals can also include, but are not limited to, farm animals (e.g., cows, pigs, horses, chickens, etc.), sport animals, pets, primates, horses, dogs, cats, mice and rats.

As used herein, the terms "treatment," "treating," and "treat" refer to any indicia of success in the treatment or amelioration of an injury, disease, or condition, including any objective or subjective parameter such as abatement; remission; diminishing of symptoms or making the injury, disease, or condition more tolerable to the subject; slowing in the rate of degeneration or decline; making the final point of degeneration less debilitating; and/or improving a subject's physical or mental well-being.

The term "pharmaceutical composition" refers to a composition suitable for administration to a subject. In general, a pharmaceutical composition is sterile, and preferably free of contaminants that are capable of eliciting an undesirable response with the subject. Pharmaceutical compositions can be designed for administration to subjects in need thereof via a number of different routes of administration, including oral, intravenous, buccal, rectal, parenteral, intraperitoneal, intradermal, intratracheal, intramuscular, subcutaneous, inhalational, and the like.

III. Diagnostic and Detection Methods

In one aspect, methods of diagnosing a subject as having Alzheimer's disease or detecting Alzheimer's disease in a subject are provided. In some embodiments, the methods described herein relate to diagnosing or detecting late-onset Alzheimer's disease. In some embodiments, the methods described herein relate to diagnosing or detecting early-onset Alzheimer's disease. In some embodiments, the methods described herein relate to diagnosing or detecting mild and/or moderate Alzheimer's disease. In another aspect, methods of detecting in a subject a set of biomarkers that have been found to be associated with Alzheimer's disease are provided.

RTKN2, MAST4, FOXO1, and APP Biomarkers

As described herein, it has been found that the expression of rhotekin 2 (RTKN2) and microtubule-associated Ser/Thr kinase 4 (MAST4) and the activity of forkhead box O1 (FOXO1) and arnyloid precursor protein (APP) are dysregulated in the brains of Alzheimer's Disease subjects. Thus, in one aspect, the disclosure provided methods of diagnosing Alzheimer's disease by detecting, in a sample from a subject, changes in levels of expression of one or both of the RTKN2 and MAST4 genes, and/or changes in the levels of activity of one or both of the FOXO1 and APP proteins as measured by the binding of the FOXO1 and APP proteins to the promoters of RTKN2 and MAST4, respectively. In some embodiments, the method comprises:

measuring in a sample from the subject one or more of (e.g., one, two, three, or four of) (i) the level of expression of RTKN2 polynucleotide (e.g., rnRNA) or protein, (ii) the level of expression of MAST4 mRNA or protein, (iii) the level of binding of FOXO1 to the RTKN2 promoter; and (iv) the level of binding of APP or a fragment thereof comprising the APP intracellular domain (AICD) to the MAST4 promoter; and comparing one or more of (e.g., one, two, three, or four of) (i) the level of expression of RTKN2 mRNA or protein, (ii) the level of expression of MAST4 mRNA or protein, (iii) the level of binding of FOXO1 to the RTKN2 promoter, and (iv) the level of binding of APP, or the fragment thereof, to the MAST4 promoter in the sample from the subject to a control sample (e.g., a healthy subject known to not have Alzheimer's disease);

wherein one or more of (e.g., one, two, three, or four of) (i) decreased expression of RTKN2, (ii) decreased expression of MAST4, (iii) increased binding of FOXO1 to the RTKN2 promoter, and (iv) decreased binding of APP, or the fragment thereof, to the MAST4 promoter in the sample from the subject, as compared to the control sample, identifies the subject as having Alzheimer's disease.

In some embodiments, once a subject has been identified as having one or more of (e.g., one, two, three, or four of) decreased expression of RTKN2, decreased expression of MAST4, increased binding of FOXO1 to the RTKN2 promoter, and decreased binding of APP or the fragment thereof to the MAST4 promoter, and has been identified as having Alzheimer's disease, the method further comprises administering one or more therapeutic interventions to the subject. In some embodiments, the therapeutic intervention is an intervention described in Section V below.

In another aspect, methods of detecting the level of expression of the biomarkers RTKN2 and MAST4 and the level of activity of the biomarkers FOXO1 and APP in a sample from a subject are provided. In some embodiments, the method comprises:

obtaining a sample from the subject; and measuring in the sample from the subject one or more of (e.g., one, two, three, or four of) (i) the level of expression of a RTKN2 polynucleotide (e.g., mRNA) or protein, (ii) the level of expression of a MAST4 polynucleotide (e,g., mRNA) or protein, (iii) the level of binding of FOXO1 to the RTKN2 promoter; and (iv) the level of binding of APP or a fragment thereof comprising the APP intracellular domain (AICD) to the MAST4 promoter.

In some embodiments, if a subject is identified as having one or more of (e.g., one, two, three, or four of) a level of expression of RTKN2 that is below a threshold level (e.g., a reference value determined for a population of healthy subjects), a level of expression of MAST4 that is below a threshold level (e.g., a reference value determined for a population of healthy subjects), a level of binding of FOXO1 to the RTKN2 promoter that is above a threshold level, and a level of binding of APP or the fragment thereof to the MAST4 promoter that is below a threshold level (e.g., a reference value determined for a population of healthy subjects), the method further comprises administering one or more therapeutic interventions to the subject. In some embodiments, the therapeutic intervention is an intervention described in Section V below.

In some embodiments, the methods comprise measuring the level of RTKN2 polynucleotide, e.g., mRNA. In some embodiments, the methods comprise measuring the level of RTKN2 protein. In some embodiments, a subject (also referred to herein as a "test subject") is diagnosed as having Alzheimer's disease (e.g., late onset Alzheimer's disease or early onset Alzheimer's disease) if the subject has a level of expression of RTKN2 mRNA or protein that is below a reference value, e.g., a reference value that is determined from the level of expression of RTKN2 mRNA or protein for a population of healthy subjects who are age-matched to the test subject. In some embodiments, a subject is diagnosed as having Alzheimer's disease if the level of RTKN2 mRNA or protein in the sample from the subject is decreased by at least 10%, at least 20%, at least 30%, at least 40%, at least 50%, at least 60%, at least 70%, at least 80%, at least 90% or more as compared to the reference value. In some embodiments, a subject is diagnosed as having Alzheimer's disease if the level of RTKN2 mRNA or protein in the sample from the subject is decreased by at least 2-fold, 3-fold, 4-fold, 5-fold, 6-fold, 7-fold, 8-fold, 9-fold, 10-fold or more as compared to the reference value.

In some embodiments, the methods comprise measuring the level of MAST4 polynucleotide, e.g., mRNA. In some embodiments, the methods comprise measuring the level of MAST4 protein. In some embodiments, a subject (or "test subject") is diagnosed as having Alzheimer's disease (e.g., late onset Alzheimer's disease or early onset Alzheimer's disease) if the subject has a level of expression of MAST4 mRNA or protein that is below a reference value, e.g., a reference value that is determined from the level of expression of MAST4 mRNA or protein for a population of healthy subjects who are age-matched to the test subject. In some embodiments, a subject is diagnosed as having Alzheimer's disease if the level of MAST4 mRNA or protein in the sample from the subject is decreased by at least 10%, at least 20%, at least 30%, at least 40%, at least 50%, at least 60%, at least 70%, at least 80%, at least 90% or more as compared to the reference value. In some embodiments, a subject is diagnosed as having Alzheimer's disease if the level of IV1AST4 mRNA or protein in the sample from the subject is decreased by at least 2-fold, 3-fold, 4-fold, 5-fold, 6-fold, 7-fold, 8-fold, 9-fold, 10-fold or more as compared to the reference value.

Measuring Polynucleotide Expression

In some embodiments, the level of polynucleotide (e.g., mRNA) expression is determined for one or both of RTKN2 and MAST4. Polynucleotide (e.g., mRNA) expression can be analyzed using routine techniques such as reverse transcription polymerase chain reaction (RT-PCR), Real-Time reverse transcription polymerase chain reaction (Real-Time RT-PCR), semi-quantitative RT-PCR, quantitative polymerase chain reaction (qPCR), quantitative RT-PCR (qRT-PCR), multiplexed branched DNA (bDNA) assay, microarray hybridization, or sequence analysis (e.g., RNA sequencing ("RNA-Seq")). Methods of quantifying polynucleotide expression are described, e.g., in Fassbinder-Orth, *Integrative and Comparative Biology*, 2014, 54:396-406; Thellin et al., *Biotechnology Advances*, 2009, 27:323-333; and Zheng et al., *Clinical Chemistry*, 2006, 52:7 (doi: 10/1373/clinchem.2005.065078).

In some embodiments, real-time or quantitative PCR or RT-PCR is used to measure the level of a polynucleotide (e.g., mRNA) in a biological sample. See, e.g., Nolan et al., *Nat. Protoc,* 2006, 1:1559-1582; Wong et al., *BioTechniques,* 2005, 39:75-75. Quantitative PCR and RT-PCR assays for measuring gene expression are also commercially available (e.g., TaqMan® Gene Expression Assays, ThermoFisher Scientific). Exemplary primer sequences for qPCR are shown in Table 1.

In some embodiments, polynucleotide (e.g., mRNA) expression is measured by sequencing. Non-limiting examples of sequence analysis include Sanger sequencing, capillary array sequencing, thermal cycle sequencing (Sears et al., *Biotechniques,* 13:626-633 (1992)), solid-phase sequencing (Zimmerman et al., *Methods Mal. Cell Biol.,* 3:39-42 (1992)), sequencing with mass spectrometry such as matrix-assisted laser desorption/ionization time-of-flight mass spectrometry (MALDI-TOF/MS; Fu et al., *Nature Biotech.,* 16:381-384 (1998)), sequencing by hybridization (Drmanac et al., *Nature Biotech.,* 16:54-58 (1998), and "next generation sequencing" methods, including but not limited to sequencing by synthesis (e.g., HiSeg™, MiSeq™, or Genome Analyzer, each available from Illumina), sequencing by ligation (e.g., SOLID™, Life Technologies), ion semiconductor sequencing (e.g., Ion Torrent™, Life Technologies), and pyrosequencing (e.g., 454™ sequencing, Roche Diagnostics). See, e.g., Liu et al., *J. Biomed Biotechnol,* 2012, 2012:251364, incorporated by reference herein. In some embodiments, polynucleotide expression is measuring using RNA-Seq technology. See, e.g., Finotello et al., *Briefings in Functional Genomics,* 2014, doi:10.1093/bfgp/elu035; and Mortazavi et al., *Nat Methods,* 2008, 5:621-628.

A detectable moiety can be used in the assays described herein (direct or indirect detection). A wide variety of detectable moieties can be used, with the choice of label depending on the sensitivity required, ease of conjugation with the probe, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, metals, and the like.

Measuring Protein Expression

In some embodiments, the level of protein expression is determined for one or both of RTKN2 and MAST4. Protein expression can be detected and quantified in a biological sample using routine techniques such as immunoassays, two-dimensional gel electrophoresis, and quantitative mass spectrometry that are known to those skilled in the art. Protein quantification techniques are generally described in "Strategies for Protein Quantitation," *Principles of Proteomics,* 2nd Edition, R, Twyman, ed., Garland Science, 2013, In some embodiments, protein expression is detected by immunoassay, such as but not limited to enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); immunofluorescence (IF); fluorescence polarization immunoassays (FPIA); and chemiluminescence assays (CL). If desired, such immunoassays can be automated. Immunoassays can also be used in conjunction with laser induced fluorescence (see, e.g., Schmaizing et al., *Electrophoresis*, 18:2184-93 (1997); Bao, *J. Chrornatogr. B. Biomed. Sci.*, 699:463-80 (1997)).

Specific immunological binding of the antibody to a protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, β-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. A urease detection system can be used with a substrate such as urea-brornocresol purple (Sigma Irnrnunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays can be automated or performed robotically, and the signal from multiple samples can be detected simultaneously. In some embodiments, the amount of signal can be quantified using an automated high-content imaging system. High-content imaging systems are commercially available (e.g., ImageXpress, Molecular Devices Inc., Sunnyvale, Calif.).

Antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. Useful physical formats comprise surfaces having a plurality of discrete, addressable locations, such as protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more protein markers for detection at each location. Surfaces may alternatively comprise one or more discrete particles (e.g., microparticles or nanoparticies) immobilized at discrete locations of a surface, where the microparticles comprise antibodies to immobilize one or more protein markers for detection.

The analysis can be carried out in a variety of physical formats. For example, the use of microtiter plates or automation could be used to facilitate the processing of large numbers of test samples.

In some embodiments, protein expression is detected by quantitative mass spectrometry, for example but not limited to, spectral count MS, ion intensities MS, metabolic labeling (e.g., stable-isotope labeling with amino acids in cell culture (SILAC), enzymatic labeling, isotopic labeling (e.g., isotope-coded protein labeling (ICPL) or isotope-coded affinity tags (ICAT)), and isobaric labeling (e.g., tandem mass tag (TMT) or isobaric tags for absolute and relative quantification (iTRAQ)). See, e.g., Bantscheff et al., *Anal Bionnal Chem*, 2012, 404:949 (doi:10.1007/s00216-0:12-6203-4); and Nikolov et al., Methods in Molecular Biology, 2012, 893:85-100.

Measuring Promoter Binding

In some embodiments, the methods comprise measuring the level of binding of FOXO1 to the RTKN2 promoter. In some embodiments, a subject (or "test subject") is diagnosed as having Alzheimer's disease (e.g., late onset Alzheimer's disease or early onset Alzheimer's disease) if the subject has a level of binding of FOXO1 to the RTKN2 promoter that is above a reference value, e.g., a reference value that is determined from the level of binding of FOXO1 to the RTKN2 promoter for a population of healthy subjects who are age-matched to the test subject. In some embodiments, a subject is diagnosed as having Alzheimer's disease if the level of binding of FOXO1 to the RTKN2 promoter in the sample from the subject is increased by at least 10%, at least 20%, at least 30%, at least 40%, at least 50%, at least 60%, at least 70%, at least 80%, at least 90% or more as compared to the reference value. In some embodiments, a subject is diagnosed as having Alzheimer's disease if the level of binding of FOXO1 to the RTKN2 promoter in the sample from the subject is increased by at least 2-fold, 3-fold, 4-fold, 5-fold, 6-fold, 7-fold, 8-fold, 9-fold, 10-fold or more as compared to the reference value.

In some embodiments, the methods comprise measuring the level of binding of APP, or the APP fragment comprising the AICD, to the MAST4 promoter. In some embodiments, a subject (or "test subject") is diagnosed as having Alzheimer's disease (e.g., late onset Alzheimer's disease or early onset Alzheimer's disease) if the subject has a level of binding of APP, or the fragment thereof, to the MAST4 promoter that is below a reference value, e.g., a reference value that is determined from the level of binding of APP or an APP fragment comprising the AICD to the MAST4 promoter for a population of healthy subjects who are age-matched to the test subject. In some embodiments, a subject is diagnosed as having Alzheimer's disease if the level of binding of APP, or the fragment thereof, to the MAST4 promoter in the sample from the subject is decreased by at least 10%, at least 20%, at least 30%, at least 40%, at least 50%, at least 60%, at least 70%, at least 80%, at least 90% or more as compared to the reference value. In some embodiments, a subject is diagnosed as having Alzheimer's disease if the level of binding of APP, or the fragment thereof, to the MAST4 promoter in the sample from the subject is decreased by at least 2-fold, 3-fold, 4-fold, 5-fold, 6-fold, 7-fold, 8-fold, 9-fold, 10-fold or more as compared to the reference value.

Methods for detecting protein-DNA interactions can be used for detecting the level of binding of FOXO1 to the RTKN2 promoter and APP to the MAST4 promoter. Suitable methods include, but are not limited to, chromatin immunoprecipitation (ChIP) coupled to PCR (e.g., quantitative PCR or quantitative real-time PCR), electrophoretic mobility shift assay (EMSA), DNAse footprinting, pull-down assay, and microplate capture and detection assay. In some embodiments, promoter binding is measured by chromatin immunoprecipitation (ChIP) coupled to PCR (e.g., qPCR or qRT-PCR), Methods of measuring promoter binding are described in the art. See, e.g., Lin et al., *Genome Res.*, 2007, 17:818-827. Exemplary primer sequences for ChIP coupled to PCR are shown in Table 1.

Additional Biomarkers

In some embodiments, the diagnostic and detection methods disclosed herein further comprise detecting for the level of expression and/or activity of one or more additional biomarkers in addition to the RTKN2, MAST4, FOXO1, and APP biomarkers discussed above.

In some embodiments, the method further comprises detecting for an increased amount of filipin in a sample (e.g., a cell sample) from the subject. Filipin is a fluorescent polyene macrolide that is used as a diagnostic tool for diseases of lipid dysregulation. It has been reported that levels of filipin in blood cells correlate with cellular damage caused by 27OHC. Additionally, it has been found that subjects having Alzheimer's disease exhibit a higher number of filipin-positive B-lymphocytes, as well as higher average mean intensity of fluorescence, as compared to control patients. See, Castello et al., *Advances in Alzheimer's Disease*, 2014, 3:137-144. Thus, filipin represents a marker that detects increased damage by 27OHC that leads to impairment of AICD-driven regulation of MAST4, FOXO1 and RTKN2, and can be used as a marker for diagnosing Alzheimer's disease and predicting risk of progressing to Alzheimer's disease (e.g., for a subject having Mild Cognitive Impairment disorder).

Methods of detecting and quantifying the amount of filipin in a sample, such as a blood sample, are described in Castello et al., supra, incorporated by reference herein. In some embodiments, the method comprises performing flow cytometry on a sample (e.g., a blood sample, e.g., a sample comprising peripheral blood mononuclear cells) to quantify the levels of filipin fluorescence. In some embodiments, a patient is diagnosed as having Alzheimer's disease if an increased number of cells in the sample from the subject exhibit filipin fluorescence, relative to a reference value (e.g., a value determined for a population of healthy subjects) or as compared to sample from a control (e.g., a healthy subject known to not have Alzheimer's disease). In some embodiments, a patient is diagnosed as having Alzheimer's disease if at least about 50%, at least about 60%, at least about 70% or more of cells in the sample from the subject exhibit filipin fluorescence.

In some embodiments, the methods of diagnosing a subject as having Alzheimer's disease further comprise measuring for the level of FOXO1 phosphorylation in the sample from the subject. FOXO1 phosphorylation can be measured, for example, by immunoassays such as Western blotting, ELISA, and the like with a phospho-specific antibody that is specific for one or more phosphorylated residues of FOXO1. In some embodiments, FOXO1 phosphorylation is measured by phosphoprotein analysis with flow cytometry. See, e.g., Krutzik et al., *Clint Immunol.*, 2004, 110: 206-221. Phospho-specific antibodies against FOXO1 are known in the art and are commercially available, e.g., from Cell Signaling Technology (Danvers, Mass.) or EMD Millipore (Billerica, MA). In some embodiments, a patient is diagnosed as having Alzheimer's disease if the level of FOXO1 phosphorylation is decreased by at least 10%, at least 20%, at least 30%, at least 40%, at least 50%, at least 60%, at least 70%, at least 80%, at least 90% or more as compared to a reference value (e.g., a value determined for a population of healthy subjects) or as compared to the level of FOXO1 phosphorylation in a control sample (e.g., a healthy subject known to not have Alzheimer's disease).

Subject Populations and Samples

In some embodiments, the test subject (i.e., the subject being assessed for Alzheimer's disease) is a human. In some embodiments, the subject is an adult human at least 30 years of age. In some embodiments, the subject is an adult human at least 65 years of age. In some embodiments, the subject is a human who has been diagnosed with Mild Cognitive Impairment or who is suspected of having Mild Cognitive Impairment.

In some embodiments, the sample from the subject comprises whole blood, serum, plasma, saliva, urine, cerebrospinal fluid, or a tissue sample (e.g., brain tissue). In some embodiments, the sample comprises blood, serum, plasma, or cerebrospinal fluid. In some embodiments, the sample is a blood sample. In some embodiments, the sample is a blood sample that comprises peripheral blood mononuclear cells.

Reference Values

In one embodiment, the level of expression of a RTKN2 or MAST4 polynucleotide (e.g., mRNA) or protein, the level of activity of FOXO1 protein or APP protein (e.g., as assessed by the level of binding of FOXO1 to the RTKN2 promoter or the level of binding of APP or a fragment comprising the AICD to the MAST4 promoter), the level of phosphorylation of FOXO1 protein, and/or the level of expression of filipin in a sample from a test subject are compared to a reference value in order to determine whether the test subject has Alzheimer's disease. A variety of methods can be used to determine the reference value for a biomarker as described herein. In one embodiment, a reference value for a particular biomarker e.g., level of expression of RTKN2) is determined by assessing the level of that particular biomarker in samples from a population of subjects that is known not to have Alzheimer's disease. As a non-limiting example, in one embodiment, the population of subjects (e.g., 10, 20, 50, 100, 200, 500 subjects or more) all are known not to have Alzheimer's disease and all are analyzed for the level of a particular biomarker (e.g., level of expression of RTKN2). In another embodiment, a reference value for a particular biomarker (e.g., level of expression of RTKN2) is determined by assessing the level of that particular biomarker in samples from a population of subjects having Mild Cognitive Impairment disorder or a particular form of Alzheimer's disease. As a non-limiting example, in one embodiment, the population of subjects (e.g., 10, 20, 50, 100, 200, 500 subjects or more) all have a mild stage of Alzheimer's disease and all are analyzed for the level of a particular biomarker (e.g., level of expression of RTKN2). In some embodiments, the population of subjects is matched to a test subject according to one or more patient characteristics such as age, sex, ethnicity, or other criteria. In some embodiments, the reference value is established using the same type of sample from the population of subjects (e.g., sample comprising blood or cerebrospinal fluid) as is used for assessing the level of the biomarker in the test subject.

The reference value may be determined using routine methods (e.g., collecting samples from subjects and determining biomarker values). Determination of particular threshold values for identifying a test subject as having Alzheimer's disease, selection of appropriate ranges, categories, stage of Alzheimer's disease, and the like are within the skill of those in the art guided by this disclosure. It will be understood that standard statistical methods may be employed by the practitioner in making such determinations. See, e.g., Principles of Biostatistics by Marcello Pagano et al. (Brook Cole; 2000); and Fundamentals of Biostatistics by Bernard Rosner (Duxbury Press, 5th Ed, 1999).

In another embodiment, the level of expression of a RTKN2 or MAST4 polynucleotide (e.g., mRNA) or protein, the level of activity of FOXO1 protein or APP protein (e.g., as assessed by the level of binding of FOXO1 to the RTKN2 promoter or the level of binding of APP or a fragment comprising the AICD to the MAST4 promoter), the level of phosphorylation of FOXO1 protein, and/or the level of expression of filipin in a sample from a test subject are compared to a control sample in order to determine whether the test subject has Alzheimer's disease. In some embodiments, a control sample is a sample from a subject who does not exhibit any clinical symptoms of Alzheimer's disease or Mild Cognitive Impairment. In some embodiments, a control sample is a sample from a subject who has been clinically diagnosed as having Mild Cognitive Impairment or as having Alzheimer's disease (e.g., a particular stage of Alzheimer's disease, e,g., mild stage Alzheimer's disease). In some embodiments, the subject from whom the control sample is obtained is the same age or about the same age as the test subject.

IV. Prognostic Methods

In another aspect, methods of identifying a subject at high risk for developing Alzheimer's disease and methods of prognosing a subject at risk of progressing to Alzheimer's disease are provided. In some embodiments, the subject has Mild Cognitive Impairment disorder (e.g., the subject has been clinical diagnosed as having Mild Cognitive Impairment disorder). In some embodiments, the method comprises detecting the level of expression and/or activity of one or more of the "brain protective" biomarkers described above (e.g., detecting the level of expression and/or activity of one, two, three, or more of these biomarkers (e.g., one, two, three, or more of the level of RTKN2 expression, the level of MAST4 expression, the level of FOXO1 binding to the RTKN2 promoter, and the level of APP binding to the MAST4 promoter).

In some embodiments, the method comprises:
detecting one or more of (i) a decreased level of expression of RTNK2 mRNA or protein, (ii) a decreased level of MAST4 mRNA or protein, (iii) an increased level of binding of FOXO1 to the RTKN2 promoter, or (iv) an increased level of binding of APP or a fragment thereof comprising the APP intracellular domain to the MAST4 promoter in a sample from the subject relative to a reference value; thereby prognosing the subject as being at risk of progressing to Alzheimer's disease.

In some embodiments, the method comprises detecting a decreased level of expression of RTNK2 mRNA or protein. In some embodiments, the method comprises detecting a decreased level of MAST4 mRNA or protein. In some embodiments, the method comprises detecting an increased level of binding of FOXO1 to the RTKN2 promoter. In some embodiments, the method comprises detecting an increased level of binding of APP or a fragment thereof comprising the APP intracellular domain to the MAST4 promoter. In some embodiments, the method comprises detecting two, three, or all four of (1), (ii), (iii), and (iv). In some embodiments, the method comprises detecting a decreased level of expression of RTKN2 mRNA or protein and further comprises detecting one or more of a decreased level of MAST4 mRNA or protein, an increased level of binding of FOXO1 to the RTKN2 promoter, or an increased level of binding of APP or a fragment thereof comprising the APP intracellular domain to the MAST4 promoter in a sample from the subject.

In some embodiments, the method comprises detecting one or more of (i) a decreased level of expression of RTNK2 mRNA or protein, (ii) a decreased level of MAST4 mRNA or protein, (iii) an increased level of binding of FOXO1 to the RTKN2 promoter, or (iv) an increased level of binding of APP or a fragment thereof comprising the APP intracellular domain to the MAST4 promoter in a sample from a subject having Mild Cognitive Impairment.

In some embodiments, the sample comprises whole blood, serum, plasma, saliva, urine, cerebrospinal fluid, or a tissue sample (e.g., brain tissue). In some embodiments, the sample comprises blood, serum, plasma, or cerebrospinal fluid. In some embodiments, the sample is a blood sample. In some embodiments, the sample is a blood sample that comprises peripheral blood mononuclear cells.

In some embodiments, the method comprises:
measuring the level of expression of RTKN2 mRNA or protein in a sample from the subject; and
comparing the level of expression of RTKN2 mRNA or protein in the sample from the subject to a reference value;
wherein decreased expression of RTKN2 in the sample from the subject, as compared to the reference value, identifies the subject as being at high risk for developing Alzheimer's disease or at risk of progressing to Alzheimer's disease.

In some embodiments, the method comprises measuring the level of RTKN2 mRNA. In some embodiments, the method comprises measuring the level of RTKN2 protein.

In some embodiments, a subject is identified as being at high risk for developing Alzheimer's disease (e.g., late onset Alzheimer's disease or early onset Alzheimer's disease) if the level of RTKN2 mRNA or protein in the sample from the subject is decreased by at least 10%, at least 20%, at least 30%, at least 40%, at least 50%, at least 60%, at least 70%, at least 80%, at least 90% or more as compared to the reference value. In some embodiments, a subject (e.g., a subject having Mild Cognitive Impairment) is identified as being at risk of progressing to Alzheimer's disease if the level of RTKN2 mRNA or protein in the sample from the subject is decreased by at least 10%, at least 20%, at least 30%, at least 40%, at least 50%, at least 60%, at least 70%, at least 80%, at least 90% or more as compared to the reference value.

In some embodiments, the method of identifying a subject at high risk for developing Alzheimer's disease or the method of prognosing a subject (e.g., a subject having Mild Cognitive Impairment) at risk of progressing to Alzheimer's disease comprises detecting the level of expression of MAST4 (e.g., mRNA or protein) in a sample from the subject. In some embodiments, the method comprises:
measuring the level of expression of MAST4 mRNA or protein in the sample from the subject; and comparing the level of expression of MAST4 mRNA or protein in the sample from the subject to a reference value;

wherein decreased expression of MAST4 in the sample from the subject, as compared to the reference value, identifies the subject as being at high risk for developing Alzheimer's disease or at risk of progressing to Alzheimer's disease.

In some embodiments, the method comprises measuring the level of MAST4 mRNA. In some embodiments, the method comprises measuring the level of MAST4 protein. In some embodiments, a subject is identified as being at high risk for developing Alzheimer's disease (e.g., late onset Alzheimer's disease or early onset Alzheimer's disease) if the level of MAST4 mRNA or protein in the sample from the subject is decreased by at least 10%, at least 20%, at least 30%, at least 40%, at least 50%, at least 60%, at least 70%, at least 80%, at least 90% or more as compared to the reference value. In some embodiments, a subject (e.g., a subject having Mild Cognitive Impairment) is identified as being at risk of progressing to Alzheimer's disease if the level of MAST4 mRNA or protein in the sample from the subject is decreased by at least 10%, at least 20%, at least 30%, at least 40%, at least 50%, at least 60%, at least 70%, at least 80%, at least 90% or more as compared to the reference value.

In some embodiments, the method of identifying a subject at high risk for developing Alzheimer's disease or the method of prognosing a subject (e.g., a subject having Mild Cognitive Impairment) at risk of progressing to Alzheimer's disease comprises detecting the level of binding of FOXO1 to the RTKN2 promoter in the sample from the subject. In some embodiments, the method comprises:

measuring the binding of FOXO1 to the RTKN2 promoter in the sample from the subject; and comparing the level of binding of FOXO1 to the RTKN2 promoter in the sample from the subject to a reference value;

wherein increased binding of FOXO1 to the RTKN2 promoter in the sample from the subject, as compared to the reference value, identifies the subject as being at high risk for developing Alzheimer's disease or at risk of progressing to Alzheimer's disease.

In some embodiments, a subject is identified as being at high risk for developing Alzheimer's disease (e.g., late onset Alzheimer's disease or early onset Alzheimer's disease) if the level of binding of FOXO1 to the RTKN2 promoter in the sample from the subject is increased by at least 10%, at least 20%, at least 30%, at least 40%, at least 50%, at least 60%, at least 70%, at least 80%, at least 90% or more as compared to the reference value. In some embodiments, a subject (e.g., a subject having Mild Cognitive Impairment) is identified as being at risk of progressing to Alzheimer's disease if the level of binding of FOXO1 to the RTKN2 promoter in the sample from the subject is increased by at least 10%, at least 20%, at least 30%, at least 40%, at least 50%, at least 60%, at least 70%, at least 80%, at least 90% or more as compared to the reference value.

In some embodiments, the method of identifying a subject at high risk for developing Alzheimer's disease or the method of prognosing a subject (e.g., a subject having Mild Cognitive Impairment) at risk of progressing to Alzheimer's disease comprises detecting the level of binding of APP, or a fragment thereof comprising the APP intracellular domain, to the MAST4 promoter in the sample from the subject. In some embodiments, the method comprises:

measuring the binding of APP or a fragment thereof comprising the APP intracellular domain to the MAST4 promoter in the sample from the subject; and comparing the level of binding of APP, or the fragment thereof, to the MAST4 promoter in the sample from the subject to a reference value;

wherein decreased binding of APP, or the fragment thereof, to the MAST4 promoter in the sample from the subject, as compared to the reference value, identifies the subject as being at high risk for developing Alzheimer's disease or at risk of progressing to Alzheimer's disease.

In some embodiments, a subject is identified as being at high risk for developing Alzheimer's disease (e.g., late onset Alzheimer's disease or early onset Alzheimer's disease) if the level of binding of APP, or the fragment thereof, to the MAST4 promoter in the sample from the subject is decreased by at least 10%, at least 20%, at least 30%, at least 40%, at least 50%, at least 60%, at least 70%, at least 80%, at least 90% or more as compared to the reference value. In some embodiments, a subject (e.g., a subject having Mild Cognitive Impairment) is identified as being at risk of progressing to Alzheimer's disease if the level of binding of APP, or the fragment thereof, to the MAST4 promoter in the sample from the subject is decreased by at least 10%, at least 20%, at least 30%, at least 40%, at least 50%, at least 60%, at least 70%, at least 80%, at least 90% or more as compared to the reference value.

In some embodiments, the methods comprise detecting the level of RTKN2 expression and further detecting (i) the level of MAST4 expression, (ii) the level of FOXO1 binding to the RTKN2 promoter, and/or (iii) the level of APP binding to the MAST4 promoter.

In some embodiments, the method comprises detecting one, two, or three of the level of RTKN2 expression, the level of MAST4 expression, the level of FOXO1 binding to the RTKN2 promoter, or the level of APP binding to the MAST4 promoter and further comprises detecting for an increased amount of filipin in a cell sample from the subject. In some embodiments, a patient is identified as being at high risk for developing Alzheimer's disease if at least about 45%, at least about 50%, or at least about 60% or more of cells in the sample from the subject exhibit filipin fluorescence.

In some embodiments, the reference value is determined as described herein, e.g., as described in Section III above. In some embodiments, the reference value is a level of a biomarker (e.g., level of RTKN2 expression, level of MAST4 expression, level of FOXO1 binding to the RTKN2 promoter, level of APP binding to the MAST4 promoter, or amount of filipin) in a sample from a subject or population of subjects that is known not to have Alzheimer's disease.

In some embodiments, for a subject (e.g., a subject having Mild Cognitive Impairment disorder) who is identified as being at risk of progressing to Alzheimer's disease, therapeutic interventions are provided. Thus, in some embodiments, for a subject who is identified as being at risk of progressing to Alzheimer's disease, the method further comprises administering one or more therapeutic interventions to the subject. In some embodiments, the therapeutic intervention is a therapeutic intervention described in Section V below. In some embodiments, the therapeutic intervention comprises a dietary modification. In some embodiments, the therapeutic intervention comprises administering one or more lipid-lowering or cholesterol-lowering medications. In some embodiments, the therapeutic intervention comprises cognitive stimulation. In some embodiments, the therapeutic intervention comprises administering a compound that increases RTKN2 expression in the subject.

V. Therapeutic Methods

In another aspect, methods of treating a subject who has been diagnosed as having Alzheimer's disease (e.g., late-onset Alzheimer's disease or early-onset Alzheimer's disease) are provided. In some embodiments, the methods described herein relate to treating mild and/or moderate Alzheimer's disease. In some embodiments, the methods comprise treating a subject by delaying or reversing the progression of Alzheimer's disease.

In some embodiments, the method comprises:
  measuring in a sample from the subject (i) the level of expression of RTKN2 mRNA or protein, (ii) the level of expression of MAST4 mRNA or protein, (iii) the level of binding of FOXO1 to the RTKN2 promoter; and (iv) the level of binding of APP or a fragment thereof comprising the APP intracellular domain (AICD) to the MAST4 promoter;
  determining that the sample from the subject has (i) a decreased level of expression of RTKN2 mRNA or protein, (ii) a decreased level of expression of MAST4 mRNA or protein, (iii) an increased level of binding of FOXO1 to the RTKN2 promoter, and (iv) a decreased level of binding of APP, or the fragment thereof, to the MAST4 promoter, as compared to a reference value; and
  administering one or more therapeutic interventions to the subject.

In some embodiments, the therapeutic intervention comprises a dietary modification. Example of dietary modifications include, but are not limited to, choosing healthier fats, reducing intake of palmitic acid, choosing foods rich in omega-3 fatty acids, increasing soluble fiber, decreasing saturated fats and trans fats, decreasing dietary sources of cholesterol, decreasing sodium intake, and decreasing alcohol consumption.

In some embodiments, the therapeutic intervention comprises administering one or more lipid-lowering or cholesterol-lowering medications. In some embodiments, the lipid-lowering or cholesterol-lowering medication is a HMG CoA reductase inhibitor (statin), an MTP inhibitor, a bile acid sequestrant, a squalene synthetase inhibitor, an oxidosqualene cyclase inhibitor, a PPAR agonist, a fibric acid derivative, nicotinic acid or a derivative thereof, an Apolipoprotein B antisense oligonucleotide, a 2-azetidione, an anti-PCSK9 antibody, or an omega 3 acid. In some embodiments, the lipid-lowering or cholesterol-lowering medication is a HMG CoA reductase inhibitor (statin). HMG CoA reductase inhibitors include, but are not limited to, atorvastatin (Lipitor), fluvastatin (Lescol), lovastatin, pitavastain (Livalo), pravastatin (Pravachol), rosuvastatin (Crestor), and sirnvastatin (Zocor).

In some embodiments, the therapeutic intervention comprises administering a compound that increases RTKN2 expression in the subject. In some embodiments, the compound increases the level of expression of RTKN2 mRNA or protein in the subject by at least 10%, at least 20%, at least 30%, at least 40%, at least 50%, at least 60%, at least 70%, at least 80%, at least 90% (e.g., as measured by testing a biological sample from the subject according to a method of detecting RTKN2 mRNA or protein expression as described herein). In some embodiments, the compound that increases the level of expression of RTKN2 mRNA or protein is a peptide, protein, oligopeptide, small organic molecule, polysaccharide, peptide, circular peptide, peptidomimetic, lipid, fatty acid, siRNA, polynucleotide, or oligonucleotide.

In some embodiments, the therapeutic intervention comprises administering a therapeutic compound identified as described in Section VI below or a structurally related analog or chemically synthesized analog thereof, or a pharmaceutical composition comprising the compound or analog thereof.

In the practice of the therapeutic methods described herein, a compound or pharmaceutical composition can be administered, for example, intravenously, intrathecally, intraspinally, intraperitoneally, intramuscularly, intranasally, subcutaneously, orally, topically, and/or by inhalation.

The compounds or pharmaceutical compositions are administered in a manner compatible with the dosage formulation, and in such amount as will be therapeutically effective. The term "therapeutically effective amount" refers to that amount of an agent (e.g., a compound or pharmaceutical composition as described herein) being administered that will treat to some extent a disease, disorder, or condition, e.g., relieve one or more of the symptoms of the disease, i.e., infection, being treated, and/or that amount that will prevent, to some extent, one or more of the symptoms of the disease, i.e., infection, that the subject being treated has or is at risk of developing. In some embodiments, a daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. The size of the dose will also be determined by the existence, nature, and extent of any adverse side-effects that accompany the administration of a particular compound in a particular patient. Determination of the proper dosage for a particular situation is within the skill of the practitioner. Frequently, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

VI. Methods of Identifying Therapeutic Compounds for the Treatment of Alzheimer's Disease In another aspect, methods of identifying therapeutic compounds for the treatment of Alzheimer's disease are provided. In some embodiments, the therapeutic compounds that are identified can be used for delaying the onset of Alzheimer's disease. In some embodiments, the therapeutic compounds that are identified can be used for delaying or reversing the progression of Alzheimer's disease. In some embodiments, the therapeutic compounds that are identified can be used for the treatment of late onset Alzheimer's disease. In some embodiments, the therapeutic compounds that are identified can be used for the treatment of early onset Alzheimer's disease.

Using the assays described herein, one can identify lead compounds that are suitable for further testing to identify those compounds that are therapeutically effective in delaying the onset or progression of Alzheimer's disease. Compounds of interest can be either synthetic or naturally-occurring. In some embodiments, the compounds of interest are screened (e.g., as an initial screen) to enrich for compounds that cross the blood-brain barrier.

The screening assays described herein can be carried out in vitro, such as by using cell-based assays, or in vivo, such as by using animal models. The screening methods are designed to screen large chemical or polymer libraries comprising, e.g., small organic molecules, peptides, peptidomimetics, peptoids, proteins, polypeptides, glycoproteins, oligosaccharides, or polynucleotides such as inhibitory RNA (e.g., siRNA, antisense RNA), by automating the assay steps and providing compounds from any convenient source to the assays, which are typically run in parallel (e.g., in microtiter formats on microtiter plates in robotic assays). In some embodiments, the screening assays utilize a high-throughput format.

Screening Assays

In some embodiments, a method of identifying a compound for the treatment of Alzheimer's disease (e.g., a compound that can be used for delaying the onset or progression of Alzheimer's disease) comprises:
  (a) contacting one or more compounds to a cell or a population of cells;
  (b) determining whether the one or more compounds increases the level of expression of rhotekin 2 (RTKN2) rnRNA or protein in the cell or population of cells, relative to a reference value or to a control sample that has not been contacted with the one or more compounds; and
  (c) selecting for the one or more compounds that increases the level of expression of RTKN2 rnRNA or protein in the cell or population of cells.

In some embodiments, the method further comprises determining whether the one or more compounds increases the level of expression of MAST4 mRNA or protein in the cell or population of cells, relative to a reference value or to a control sample that has not been contacted with the one or more compounds, and selecting for the one or more compounds that increases the level of expression of MAST4 mRNA or protein in the cell or population of cells.

In some embodiments, the selecting step comprises selecting for the one or more compounds that increase the level of expression of RTKN2 mRNA or protein and/or increases the level of expression of MAST4 mRNA or protein in the cell or population of cells by at least 10%, at least 20%, at least 30%, at least 40%, at least 50%, at least 60%, at least 70%, at least 80%, at least 90% or more relative to the reference value or control sample. In some embodiments, the selecting step comprises selecting for the one or more compounds that increase the level of expression of RTKN2 mRNA or protein and/or increases the level of expression of MAST4 mRNA or protein in the cell or population of cells by at least 2-fold, at least 3-fold, at least 4-fold, at least 5-fold, at least 6-fold, at least 7-fold, at least 8-fold, at least 9-fold, at least 10-fold or higher relative to the reference value or control sample.

In some embodiments, measuring induction of mRNA or protein expression or activity involves determining the level of polynucleotide or polypeptide expression or activity in a cell or population of cells that has been contacted with the compound and comparing the level to a baseline or range. Typically, the baseline value is representative of the expression or activity of the polynucleotide or polypeptide in a biological sample that has not been contacted with the compound. Methods of detecting and quantifying mRNA or protein expression are described in Section III above.

Measuring Response to Stress Stimuli

In some embodiments, the methods of identifying compounds for the treatment of Alzheimer's disease further comprise a step of screening compounds (e.g., compounds that were identified as increasing the level of expression of RTKN2 mRNA or protein and/or increasing the level of expression of MAST4 mRNA or protein in the cell or population of cells) for response to one or more stress stimuli. Thus, in some embodiments, the screening method further comprises:
  subjecting the cell or population of cells to one or more stress stimuli; and
  selecting the one or more compounds that increase cell survival, relative to a reference value or to a control sample that has not been contacted with the one or more compounds.

In some embodiments, the stress stimulus is oxysterol. In some embodiments, the stress stimulus is pairnitic acid. In some embodiments, a compound is identified as a compound that increases cell survival if the percentage of cells that survive when subjected to the stress stimulus is increased by at least 10%, at least 20%, at least 30%, at least 40%, at least 50%, at least 60%, at least 70%, at least 80%, at least 90% or more relative to the reference value or to the control sample that is subjected to the stress stimulus in the absence of the compound. In some embodiments, the compound is one that increases cell survival to at least the same extent as a known positive control for increasing cell survival in the presence of a stress stimulus (e.g., 27-hydroxycholesterol).

Cells for Screening Assays

The screening assays described herein may be practiced in any of a number of cell types or cell populations. In some embodiments, the cell or population of cells is a mammalian cell. In some embodiments, the cell or population of cells is a human cell. In some embodiments, the cell or population of cells is from brain, nervous tissue, thyroid, eye, skeletal muscle, cartilage, kidney, lung, liver, heart, or bone tissue, or from blood, serum, plasma, or cerebrospinal fluid. In some embodiments, the cell or population of cells comprises hippocampal cells, neurons, stem cells, embryonic stem cells, pluripotent stem cells, or induced pluripotent stem cells. In some embodiments, the cells are primary cells. In some embodiments, the cells are from a transformed cell line.

In some embodiments, the cell or population of cells is from an animal model of Alzheimer's disease. Animal models of Alzheimer's disease, as well as cell cultures obtained from animal models of Alzheimer's disease, are described in the art. See, e.g., Trinchese et al., *J Mol Neurosci*, 2004, 24:15-21; and LaFerla et al., *Cold Spring Harb Perspect Med*, 2012 Nov. 1, doi: 10.1101/cshperspect.a006320; see also, U.S. Patent Publication No. 2005/0172344, incorporated by reference herein. In some embodiments, the animal model (e.g., for obtaining cells or populations of cells or for an in vivo model) is a SAMP8 mouse model, which is an accelerated aging model that presents with memory deficits. See, Yagi et al., *Brain Res.*, 1998, 474:86-93; Takeda et al., *J. Amer. Geriatr. Soc.*, 1991, 39:911-919.

In some embodiments, the cell or population of cells is from a subject having Alzheimer's disease. In some embodiments, the cell or population of cells is from a subject having Mild Cognitive Impairment disorder.

Chemical Compounds and Compound Libraries

Essentially any chemical compound can be tested for its ability to increase the level of expression of RTKN2 and/or MAST4, and optionally to increase cell survival in response to stress stimuli, in a cell or population of cells. In some embodiments, the compound is one that can be dissolved in aqueous or organic solutions. It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland), as well as providers of small organic molecule and peptide libraries ready for screening, including Chembridge Corp. (San Diego, Calif.), Discovery Partners International (San Diego, Calif.), Triad Therapeutics (San Diego, Calif.), Nanosyn (Menlo Park, Calif.), Affymax (Palo Alto, Calif.), ComGenex (South San Francisco, Calif.), Tripos, Inc. (St. Louis, Mo.); and Selleckchem (Houston, Tex.

Representative amino acid compound libraries include, but are not limited to, peptide libraries (see, e.g., U.S. Pat. Nos. 5,010,175; 6,828,422; and 6,844,161; Furka, *Int. J. Pept. Prot. Res.*, 37:487-493 (1991); Houghton et al., *Nature*, 354:84-88 (1991); and Eichler, *Comb Chem High Throughput Screen.*, 8:135 (2005)), peptoids (PCI Publication No, WO 91/19735), encoded peptides (PCT Publication No. WO 93/20242), random bio-oligomers (PCT Publication No. WO 92/00091), vinylogous polypeptides (Hagihara et al., *J. Amer. Chem. Soc.*, 114:6568 (1992)), nonpeptidal peptidornirnetics with β-D-glucose scaffolding (Hirschmann et al., *J. Amer. Chem. Soc.*, 114:9217-9218 (1992)), peptide nucleic acid libraries (see, e.g., U.S. Pat. No. 5,539,083), antibody libraries (see, e.g., U.S. Pat. Nos. 6,635,424 and 6,555,310; PCT Application No. PCT/US96/10287; and Vaughn et al., *Nature Biotechnology*, 14:309-314 (1996)), and peptidyi phosphonates (Campbell et al., *J. Org. Chem.*, 59:658 (1994)).

Representative nucleic acid compound libraries include, but are not limited to, genomic DNA, cDNA, mRNA, inhibitory RNA (e.g., RNAi, siRNA), and antisense RNA libraries. See, e.g., Ausubel, *Current Protocols in Molecular Biology*, eds. 1987-2005, Wiley Interscience; and Sambrook and Russell, *Molecular Cloning: A Laboratory Manual*, 2000, Cold Spring Harbor Laboratory Press. Nucleic acid libraries are described in, for example, U.S. Pat. Nos. 6,706,477; 6,582,914; and 6,573,098. cDNA libraries are described in, for example, U.S. Pat. Nos. 6,846,655; 6,841, 347; 6,828,098; 6,808,906; 6,623,965; and 6,509,175. RNA libraries, for example, ribozyme, RNA interference, or siRNA libraries, are described in, for example, Downward, *Cell*, 121:813 (2005) and Akashi et al., *Nat. Rev. Mol. Cell Biol.*, 6:413 (2005). Antisense RNA libraries are described in, for example, U.S. Pat. Nos. 6,586,180 and 6,518,017.

Representative small organic molecule libraries include, but are not limited to, diversomers such as hydantoins, benzodiazepines, and dipeptides (Hobbs et al., *Proc. Nat. Acad. Sci. USA*, 90:6909-6913 (1993)); analogous organic syntheses of small compound libraries (Chen et al., *J. Amer. Chem. Soc.*, 116:2661 (1994)); oligocarbamates (Cho et al., *Science*, 261:1303 (1993)); benzodiazepines (e.g., U.S. Pat. No. 5,288,514; and Baum, *C&EN*, January 18, page 33 (1993)); isoprenoids (e.g., U.S. Pat. No. 5,569,588); thiazolidinones and metathiazanones (e.a., U.S. Pat. No. 5,549, 974); pyrrolidines (e.g., U.S. Pat. Nos. 5,525,735 and 5,519, 134); morpholine compounds (e.g., U.S. Pat. No. 5,506, 337); tetracyclic benzimidazoles (e.g., U.S. Pat. No. 6,515, 122); dihydrobenzpyrans (e.g., U.S. Pat. No. 6,790,965); amines (e.g., U.S. Pat. No. 6,750,344); phenyl compounds (e.g., U.S. Pat. No. 6,740,712); azoles (e.g., U.S. Pat. No. 6,683,191); pyridine carboxamides or sulfonamides (e.g., U.S. Pat. No. 6,677,452); 2-aminobenzoxazoles (e.g., U.S. Pat. No. 6,660,858); isoindoles, isooxyindoles, or isooxyquinolines (e.g., U.S. Pat. No. 6,667,406); oxazolidinones (e.g., U.S. Pat. No. 6,562,844); and hydroxylamines (e.g., U.S. Pat. No. 6,541,276).

Devices for the preparation of combinatorial libraries are commercially available. See, e.g., 357 MPS and 390 MPS from Advanced Chem. Tech (Louisville, Ky.), Symphony from Rainin Instruments (Woburn, Mass.), 433A from Applied Biosystems (Foster City, Calif.), and 9050 Plus from Millipore (Bedford, Mass.).

Optimization of Compounds

In some embodiments, after candidate compounds for the treatment of Alzheimer's disease are identified by the screening assays described above as, compound optimization is conducted. Typically, optimization involves the use of in vitro and in viva screens (e.g., in an appropriate animal model, e.g., a mammal such as a mouse, rat, or monkey) to assess the biological, pharmacokinetic, and pharmacodynamic properties of the compounds, such as oral bioavailability, half-life, metabolism, toxicity, pharmacokinetic profile, and pharmacodynamic activity. See, e.g., Guido et al., *Combinatorial Chemistry & High Throughput Screening*, 2011, 14:830-839; and Ghose et al., *ACS Chem Aieurosci*, 2012, 3:50-68. In some embodiments, structural analogs of a candidate compound are designed and screened. Methods of designing and screening structural analogs are described in the art. See, e.g., Dimova et al., *Med. Chem. Commun.*, 2016, 7:859-863; and Analogue-Based Drug Discovery II, J. Fischer and C. R. Ganellin, eds., Wiley-Val Verlag GmbH & Co., KGaA, Weinheim, Germany, 2010.

In some embodiments, a compound that is identified by the screening assays described herein, or a structurally related analog thereof, is used for the preparation of a pharmaceutical composition for use in the treatment of Alzheimer's disease (e.g., for delaying the onset or progression of Alzheimer's disease). The pharmaceutical composition will typically comprise the compound (e.g., the compound identified by the screening assays described herein or a structurally related analog thereof) and one or more pharmaceutically acceptable carriers and/or pharmaceutically acceptable excipients. As used herein, "pharmaceutically acceptable carrier" or "pharmaceutically acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Compositions comprising such carriers are formulated by well-known conventional methods (see, for example, Remington, The Science and Practice of Pharmacy, $22^{nd}$ edition, Allen, Lloyd V., Jr., ed., Pharmaceutical Press, 2013).

VII. Examples

The following examples are offered to illustrate, but not to limit, the claimed invention.

Example 1

The biological function of the amyloid precursor protein (APP) in the brain remains unresolved, a significant shortcoming that hinders our understanding of the complex etiology of late-onset Alzheimer's disease (AD) (1-5). Several laboratories, including ours, have proposed that APP could function instead as part of an adaptive response against bona fide pathogenic triggers of late-onset AD, such as oxidative stress, infection/inflammation and cholesterol dysregulation (4, 6-8). Nevertheless, while there is descriptive evidence consistent with such an adaptive response role, there is little mechanistic evidence to support it. The aim of this study was to determine whether APP regulates such an adaptive response to the cholesterol oxidized metabolite 27-hydroxycholesterol (27OHC), an early marker of cholesterol dysregulation in the AD brain that causes AD-like pathology both in vitro and in vivo (9, 10), and whether such a response could be mechanistically linked to late-onset AD pathogenesis.

We report that in cultured cells, APP is necessary to mount a hormetic adaptive response to 27OHC cytotoxicity. In-depth transcriptome analysis from $App^{wt}$ and $App^{ko}$ mouse cerebral cortices and chromatin immunoprecipitation assays allowed us to elicit the molecular cascade that drives this adaptive response, in which the transcriptional activity of the APP intracellular domain (AICD) ultimately results in the FOXO1-dependent upregulation of the oxysterol stress responder RTKN2 to optimize cell viability. At higher, non-hormetic doses of 27OHC, the AICD-driven pathway does not engage, resulting in downregulation of RTKN2 and higher cytotoxicity. We further show that this pathway is impaired in the brain of a mouse model of dyslipidemia associated with cognitive impairment and higher levels of 27OHC, as well as in the brain of late-onset AD patients. Notably, the pathway is not altered in the brain of patients with frontotemporal dementia, a neurodegenerative disease not primarily associated with dyslipidemia or oxysterol dysregulation. Our findings unveil a previously unknown function of APP and provide a novel conceptual framework that could lead to a deeper understanding of APP function in the healthy and demented brain, potentially leading to novel evidence-based approaches to therapy.

APP Mediates a Hormetic Response to 27OHC

Figure 1B:
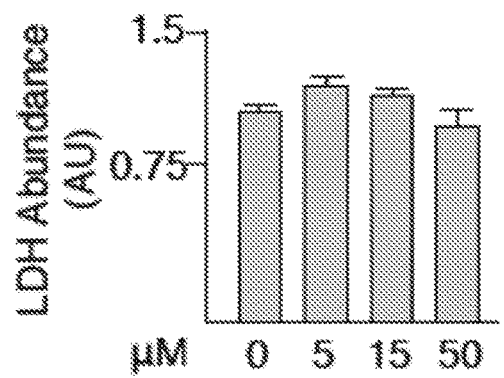
Figure 1C:
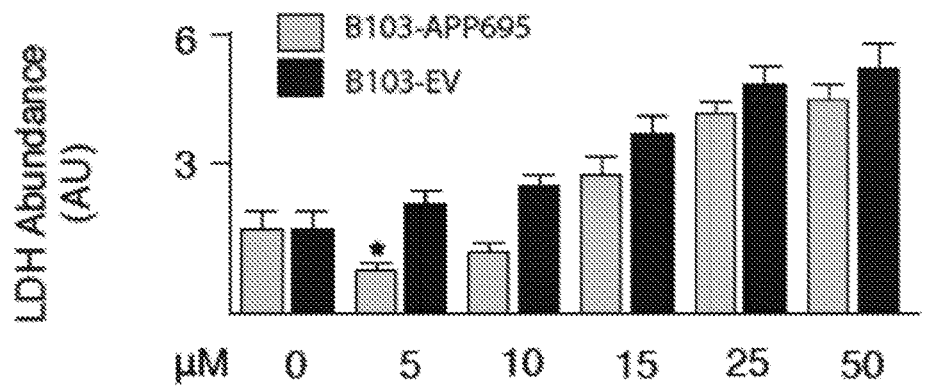
Figure 1D:
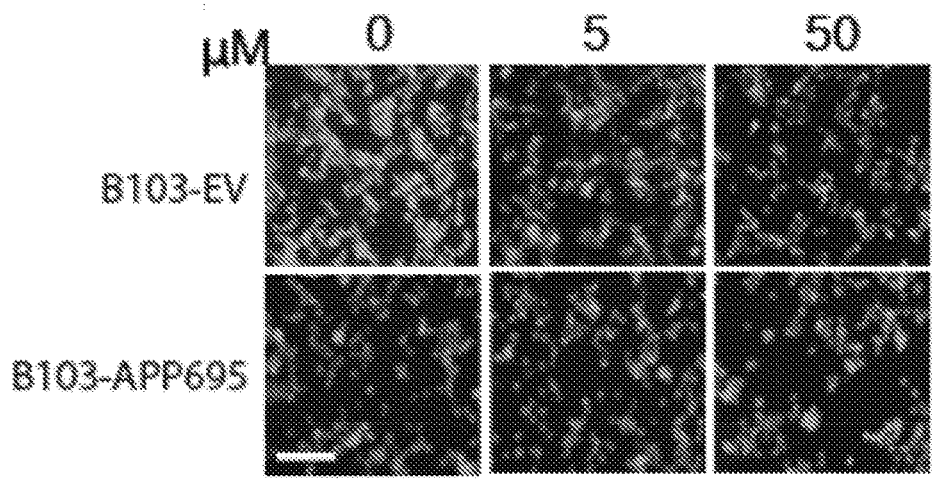

To determine the effect of 27OHC on cell viability, we treated neuron-differentiated SH-SY5Y cells with increasing concentrations of 27OHC and measured the levels of lactate dehydrogenase (LDH) as an indication of cell viability. As illustrated in FIG. 1A, 27OHC elicited a biphasic dose-dependent cellular response that appears hormetic in nature (11), such that low levels elicit a stress response that optimizes cellular homeostasis with a maximum protective effect observed at 5 µM and increasing cytotoxicity at 15, 25, and 50 µM treatments. 24-hydroxycholesterol (24OHC), used as an oxysterol control, had no effect (FIG. 1B). To determine the influence of APP on the cell survival response to 27OHC, we transfected B:103 cells, a CNS rat neural cell line that does not express APP (10), either with the 695 amino acid isoform of APP ($APP_{695}$) or with control empty vector, and measured cell viability also as determined by LDH levels. In the absence of APP, 27OHC increased LDH levels in a dose-dependent manner. By contrast, the presence of APP led to a biphasic response comparable to that shown by SH-SY5Y cells, in which 5 µM 27OHC reduced LDH levels, whereas doses greater than 10 µM were dose-dependently cytotoxic (FIG. 1C). To confirm that LDH levels are altered because of an increase in cell death, we analyzed dead/live cell abundance in response to 5 µM and 50 µM 27OHC in the presence or absence of APP. Consistent with LDH data, 27OHC was protective in APP-expressing cells but not those transfected with empty vector (FIG. 1D-1E).

Figure 1H:
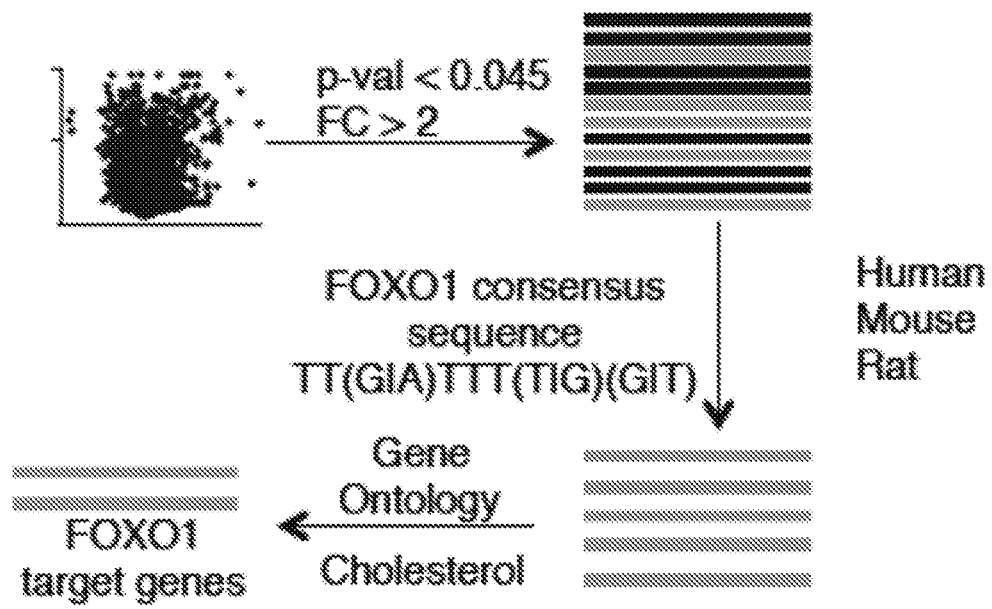
Figure 1I:
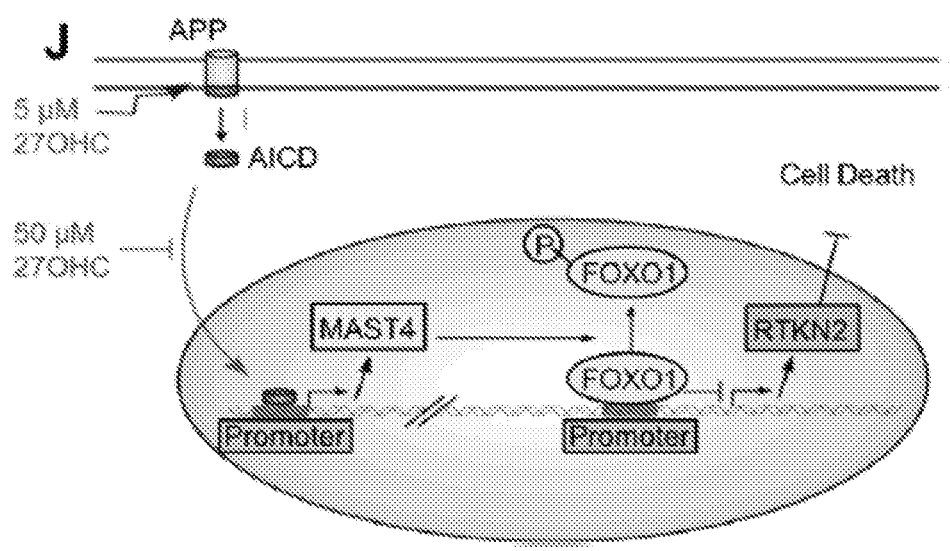

We next asked whether the molecular mechanism mediating the APP effect on the cell viability response to 27OHC could occur directly through the transcriptional activity of its intracellular domain, AICD. To search for AICD transcriptional targets that are modulated in response to 27OHC, we first generated microarray transcriptomes from cerebral cortex of 3-week old $App^{ko}$ and control ($App^{wt}$) mice and utilized a volcano plot to identify differentially expressed genes (FIG. 1F). Amongst those with the greatest fold change and lowest p-values, MAST4 (microtubule-associated Ser/Thr kinase family member 4) was the most dramatically downregulated gene in the $App^{ko}$ brain (FIG. 1G). MAST4 is upregulated in response to neuronal stress and is highly expressed in the brain (12) and therefore is a plausible candidate as a stress response mediator modulated by AICD. The specific function of MAST4 has not been reported, but it is predicted to be a Serine/Threonine kinase (13). To create a physiological context for MAST4 pertinent to oxysterol regulation, we chose a strategy delineated in FIG. 1H. We first queried the string database for MAST4-interacting proteins string-db,org). Amongst the candidates identified, FOXO1 is predicted to associate with MAST4. FOXO1 is a transcription factor that regulates a diverse set of subcellular systems in response to cellular stress (14, 15) and, of particular interest, it is a shared mediator of both insulin and leptin signaling, whose impairment leads to hypercholesterolemia, obesity and health risks associated with it, including late-onset AD (16, 17). Thus, we searched for downstream transcriptional targets of FOXO1 whose expression is differentially regulated in the absence of APP, selected transcripts with a p-value<0.045 and a fold change>2 from our $App^{ko}$ and $App^{wt}$ cerebral cortex transcriptome datasets, and queried their promoter sequences +/-2000 bp from the transcriptional start site to identify promoters containing a FOXO1 consensus sequence conserved across human, mouse, and rat. Of the promoters identified, we sorted them further based on their predicted participation in cholesterol metabolism (FIG. 1H). Of the identified transcripts, rhotekin 2 (RTKN2) showed the greatest differential expression with the greatest level of significance, Critically, RTKN2 is necessary to elicit a cell stress response to oxysterol cytotoxicity, consistent with a potential role in oxysterol signaling in the brain (21-23). Based on these data, a working model was generated for an APP-driven hormetic response to 27OHC. This model, which is illustrated in FIG. 1I, proposes that low doses, but not high doses, of 27OHC elicit an AICD-driven transactivation of MAST4, leading to phosphorylation and inhibition of FOXO1 transcriptional repression of RTKN2 to optimize cell survival.

AICD Regulates MAST4 in Response to 27OHC

Figure 2A:
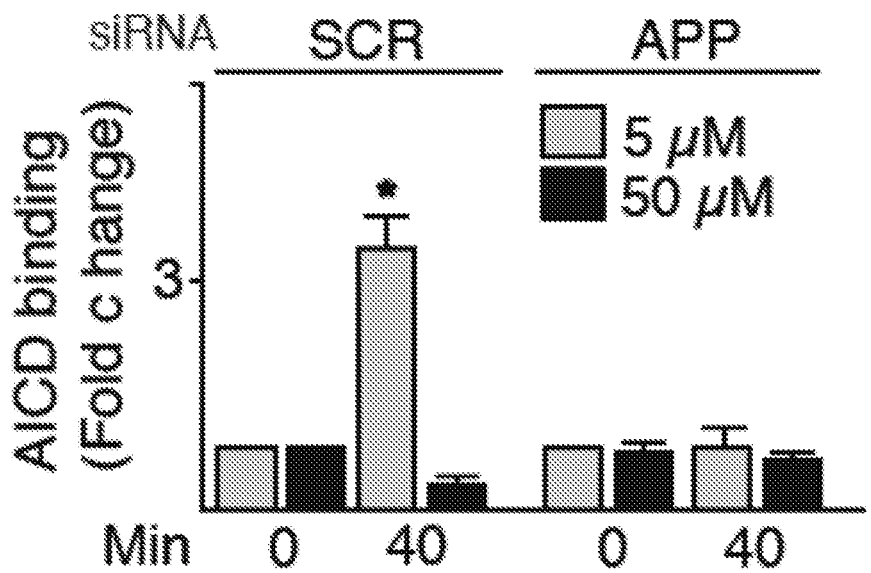
FIG. 2A-FIG. 2G. AICD binds to the MAST4 promoter in response to hormetic concentrations of 27OHC to increase MAST4 mRNA and protein expression (A-C) ChIP assays for the binding of AICD to the MAST4 promoter in neuron-differentiated SH-SY5Y cells transfected with control or APP siRNA (A), in B103 cells transfected with APP$_{695}$ or APP$_{G700A}$ (B), and in rat cortical neurons (C). (D-F) MAST4 mRNA in neuron-differentiated SH-SY5Y cells (D), B103 cells transfected with APP$_{695}$ or APP$_{G700A}$ (E) and rat cortical neurons (F). (G) MAST4 protein expression in neuron-differentiated SH-SY5Y cells in response to 27OHC, with or without APP siRNA.
Figure 2B:
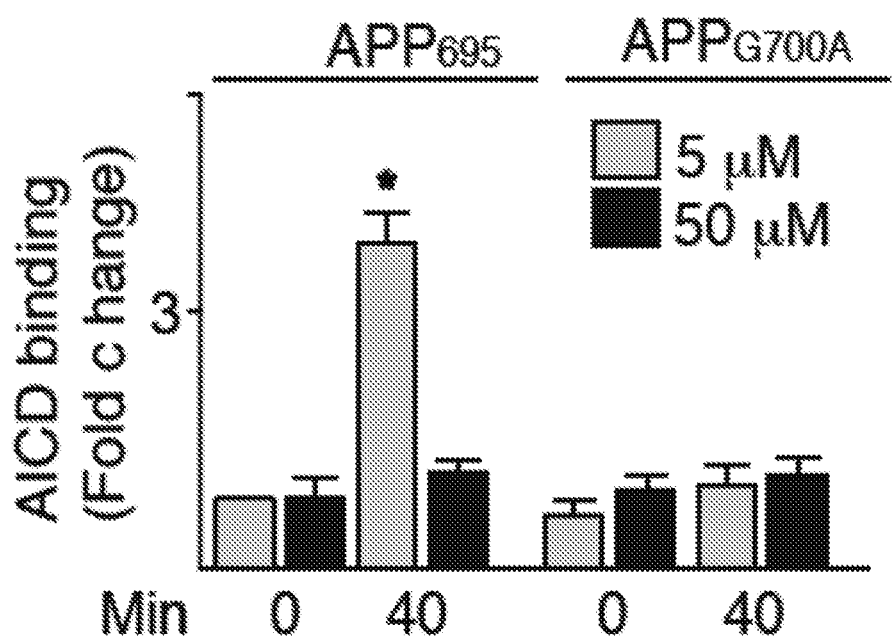
Figure 2C:
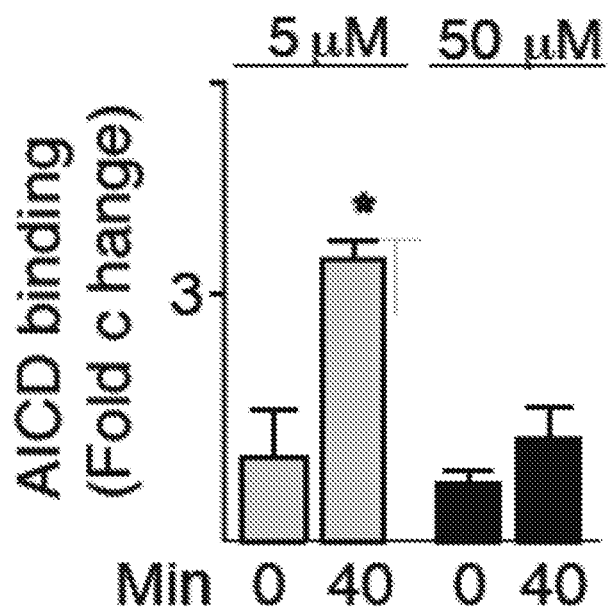
Figure 2D:
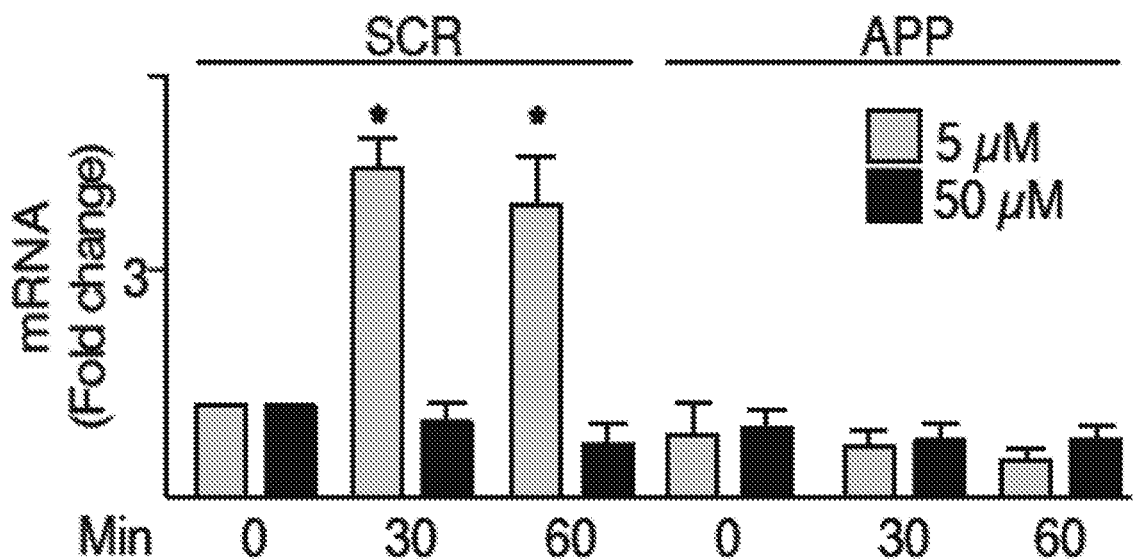
Figure 2E:
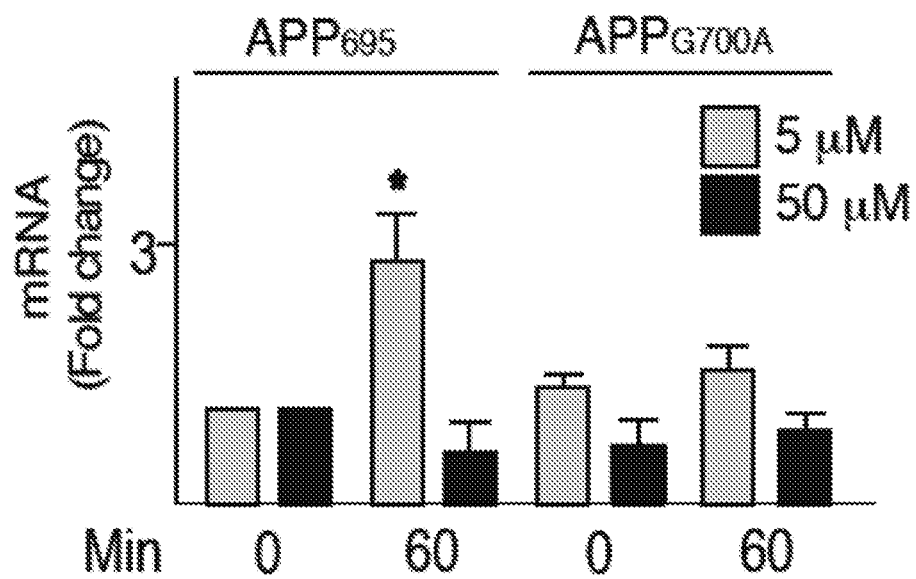
Figure 2F:
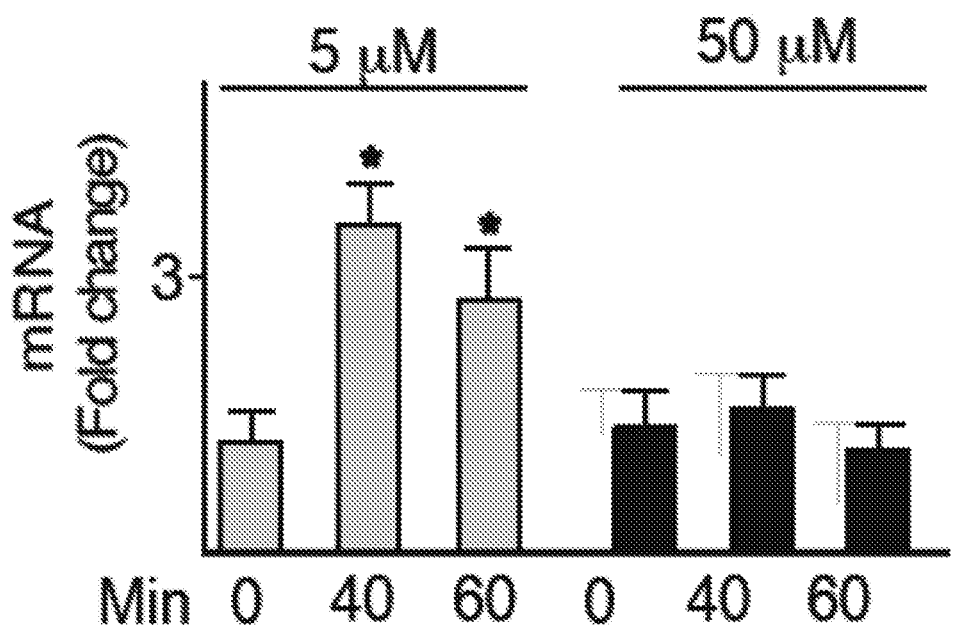
Figure 2G:
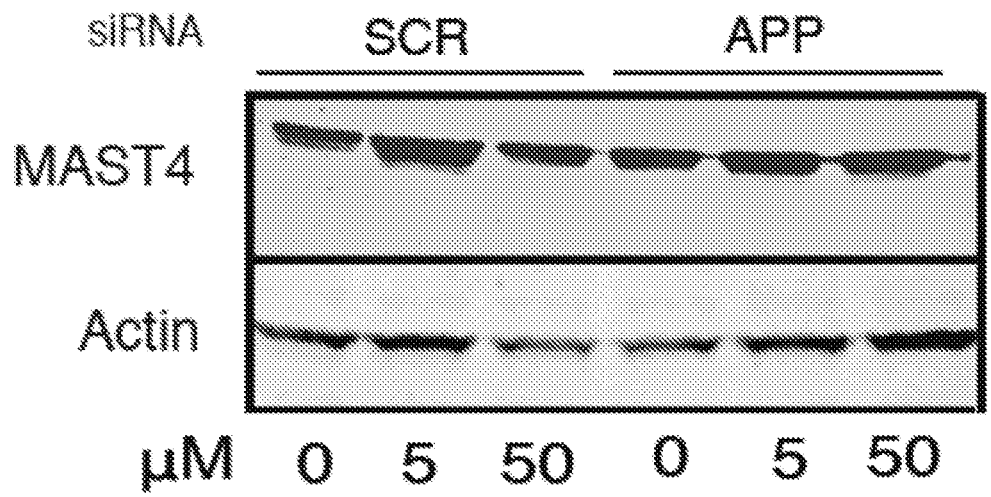

To test for a potential involvement of MAST4, FOXO1 and RTKN2 in an APP-driven adaptive response to 27OHC, we first determined whether MAST4 is indeed an AICD target by carrying out chromatin immunoprecipitation (ChIP) of AICD from neuron-differentiated SH-SY5Y cells, in the presence and absence of 27OHC. FIG. 2A shows that AICD does bind to the MAST4 promoter in the presence of cytoprotective 5 µM 27OHC, but not cytotoxic 50 µM. Binding was not increased upon APP siRNA knockdown (FIG. 2A). Next, because APP has a cholesterol-sensing domain that is known to bind both cholesterol and oxysterols (12), we reasoned that disrupting the integrity of this domain could prevent the APP adaptive response to 27OHC. Therefore, we carried out ChIP in APP-null B103 cells transfected with the wild-type 695 amino acid form of APP ($APP_{695}$) or with APP harboring the G700A mutation ($APP_{G700A}$), which has been shown to abrogate its cholesterol sensing function (14). $APP_{G700A}$ does not partition into cholesterol-rich lipid rafts (not shown), as expected (12), and otherwise shows no measurable differences in APP metabolism, FIG. 2B shows increased AICD binding to the MAST4 promoter in B103 cells transfected with $APP_{695}$ in response to 5 µM 27OHC, but not to 50 µM, an effect not seen in cells expressing $APP_{G700A}$, indicating that the cholesterol-sensing domain of APP is indeed necessary for the binding of AICD to the MAST4 promoter in response to 27OHC. Finally, as shown in FIG. 2C, AICD also interacts with the MAST4 promoter in primary rat cortical neurons treated with 5 µM 27OHC, but not to 50 µM 27OHC (FIG. 2C). Next, we assessed the transcriptional effect of AICD on MAST4. FIG. 2D-2F show that the binding of AICD to the MAST4 promoter coincides with elevated MAST4 mRNA levels in response to 5 µM but not 50 µM 27OHC, also dependent on the cholesterol-sensing domain of APP (FIG. 2E), and also present in rat primary neurons (FIG. 2F). Furthermore, MAST4 protein expression increased in neuron-differentiated SH-SY5Y cells response to 5 µM but not 50 µM 27OHC or following APP knockdown (FIG. 2G). Thus, AICD binds to the MAST4 promoter leading to higher MAST4 mRNA and protein expression in response to the cytoprotective 5 µM 27OHC, but not to the cytotoxic 50 µM dose. This signaling event is absent upon mutagenesis of the APP cholesterol binding domain.

MAST4 Regulates RTKN2 Expression Through FOXO1

Figure 3A:
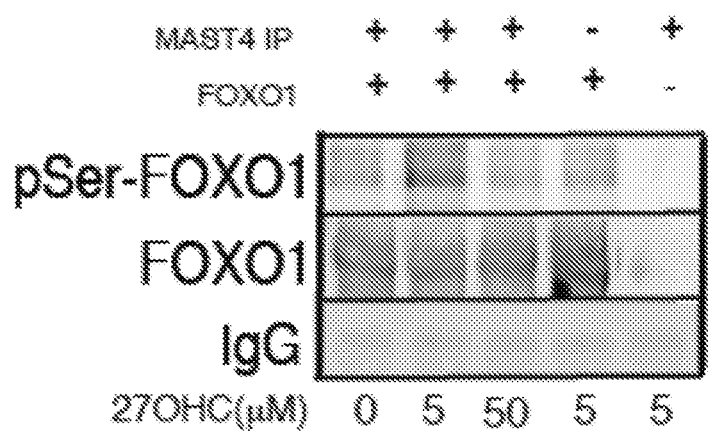
FIG. 3A-FIG. 3J. MAST4 kinase regulates FOXO1 binding to the RTKN2 promoter in response to 5 μM 27OHC to increase RTKN2 mRNA. (A) Representative Western blot of FOXO1 and pSer-FOXO1 in immunoprecipitates of MAST4 from neuron-differentiated SH-SY5Y cells treated with 0, 5, or 50 µM 27OHC. No increase in pSer-FOXO1 occurred in response to 50 µM 27OHC or in IgG control immunoprecipitates. No pSer-FOXO1 was detected in the absence of recombinant FOXO1. (B) Schematic diagram of MAST4 domain architecture. A putative kinase-null mutant was generated by E682A site-directed mutagenesis.
Figure 3B:
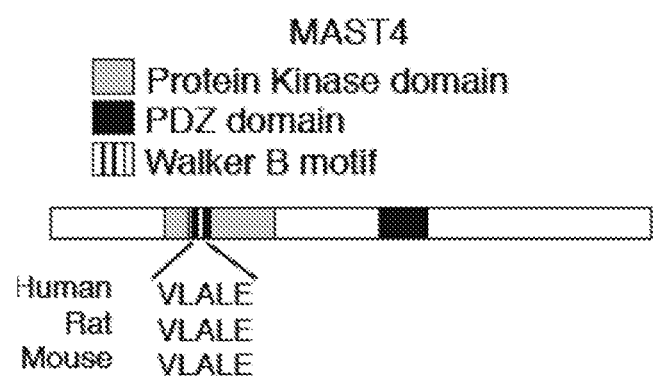
Figure 3C:
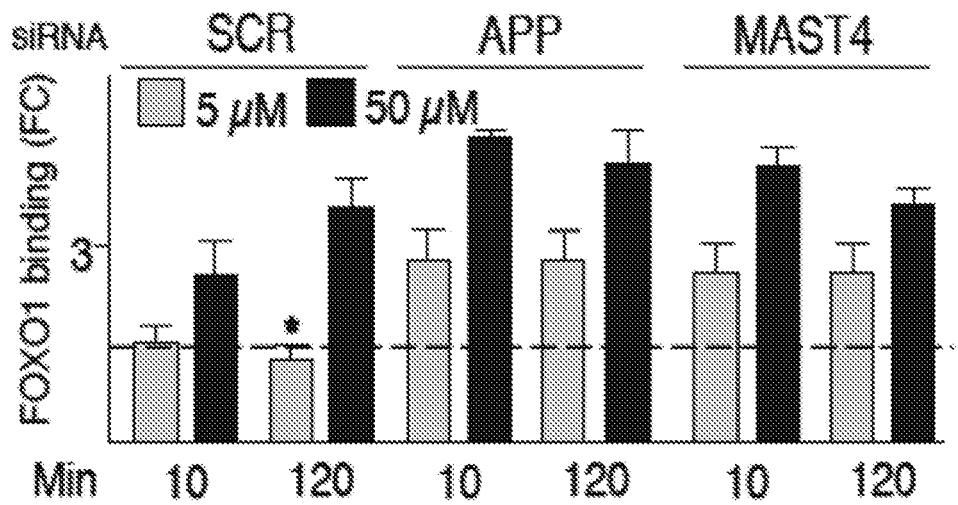
Figure 3D:
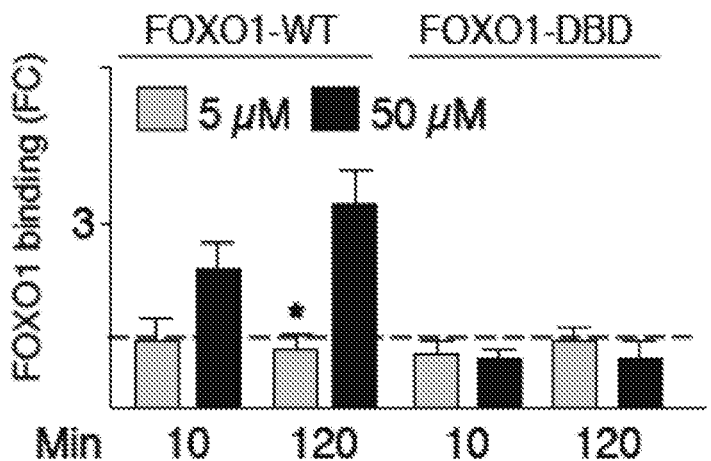
Figure 3E:
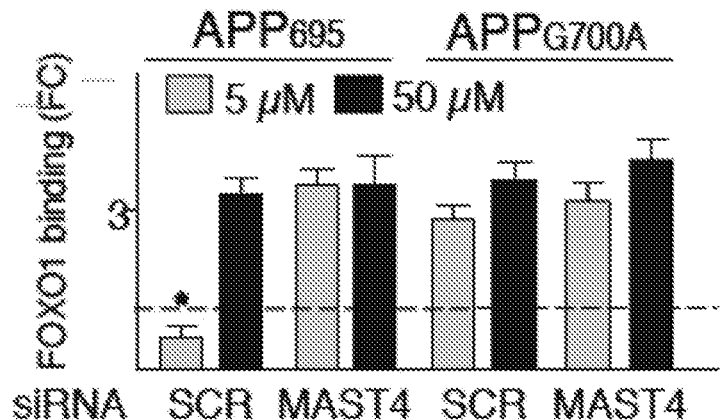
Figure 3F:
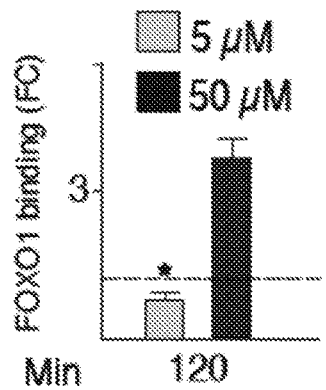

Next, we determined whether MAST4 is a bona fide kinase of FOXO1, with which it is predicted to associate. We conducted in vitro kinase assays with recombinant FOXO1 and immunoprecipitated MAST4 from lysates derived from cells treated with 0, 5, or 50 µM 27OHC. Increased FOXO1 phosphorylation was observed in MAST4 immunoprecipitates from cells treated with 5 µM but not 50 µM 27OHC (FIG. 3A). We then confirmed the dependence of FOXO1 phosphorylation on the MAST4 kinase activity by generating a kinase-null MAST4 mutant. Sequence analysis of MAST4 reveals a serineithreonine kinase domain containing a walker-B motif with an adjacent aspartic residue, a chemical signature associated with ATP binding and catalysis of phosphorylation (FIG. 3B) (15). To create a kinase-null MAST4 mutant, we substituted wild-type glutamic acid at codon 682, adjacent to the Walker-B motif, with alanine, to generate $MAST4_{E632A}$. Immunoprecipitates of $MAST4_{E682A}$ did not phosphorylate FOXO1 (not shown). Next, we determined whether FOXO1 binds to the RTKN2 promoter and whether that binding may be modulated in response to 27OHC exposure, ChIP in neuron-differentiated SH-SY5Y cells confirmed the binding of FOXO1 to the RTKN2 promoter and the decrease of that binding upon exposure to 5 µM 27OHC but not 50 µM 27OHC or following APP or MAST4 knockdowns (FIG. 3C). Expression of a dominant negative form of FOXO1 lacking the transactivation domain (FOXO1-DBD) led to increased binding (FIG. 3D). Furthermore, FOXO1 binding was also decreased in response to 5 µM 27OHC in B103 expressing $APP_{695}$ but not $APP_{G700A}$ or in cells treated with 50 µM 27OHC (FIG. 3E). These results were confirmed in rat cortical neurons (FIG. 3F).

Figure 3G:
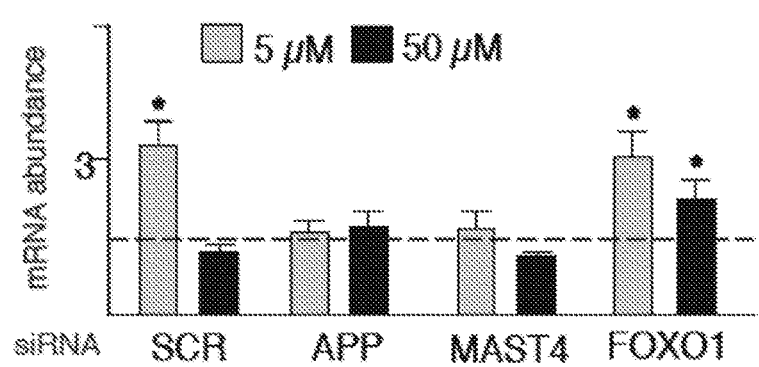
Figure 3H:
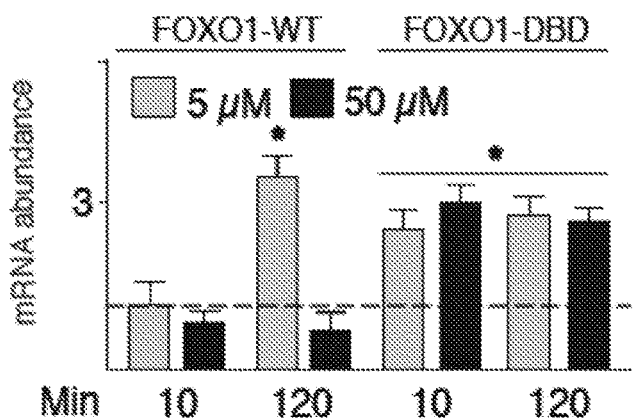
Figure 3I:
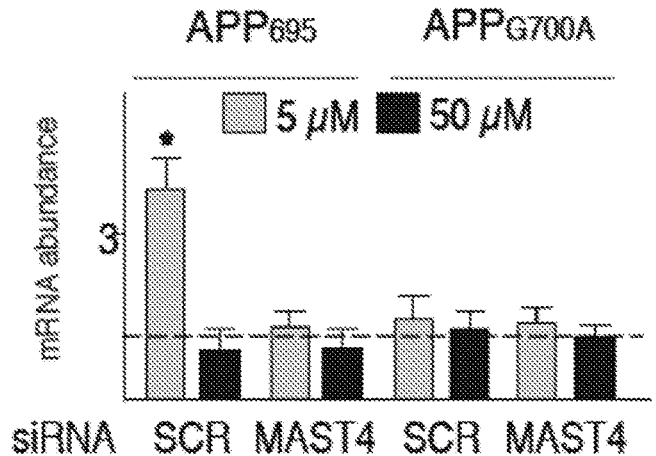
Figure 3J:
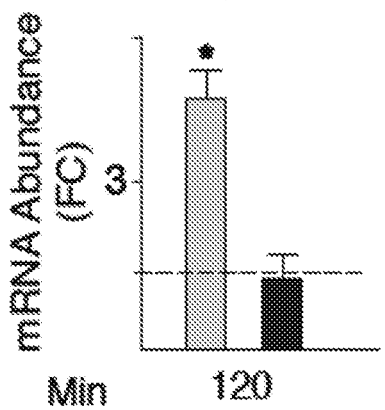

Next, to determine the effect of FOXO1 on the transcription of RTKN2, we transfected neuron-differentiated SH-SY5Y cells with control, APP, MAST4, or FOXO1 siRNAs and treated them with 5 or 50 µM 27OHC before measuring RTKN2 mRNA. As illustrated in FIG. 3G, 5 µM but not 50 µM 27OHC increased RTKN2 mRNA but not if APP or MAST4 were knocked down. RTKN2 mRNA was also elevated in FOXO1 siRNA-transfected cells (FIG. 3G). Furthermore, consistent with the lack of binding of FOXO1-DBD to the RTKN2 promoter, RTKN2 mRNA increases upon FOXO1-DBD expression (FIG. 3H). In B103 cells, RTKN2 was upregulated in the presence of $APP_{695}$ after treatment with 5 µM 27OHC but not upon expression of $APP_{G700A}$ or in cells treated with 50 µM 27OHC (FIG. 3I). These results were confirmed in rat cortical neurons (FIG. 3J).

Figure 4A:
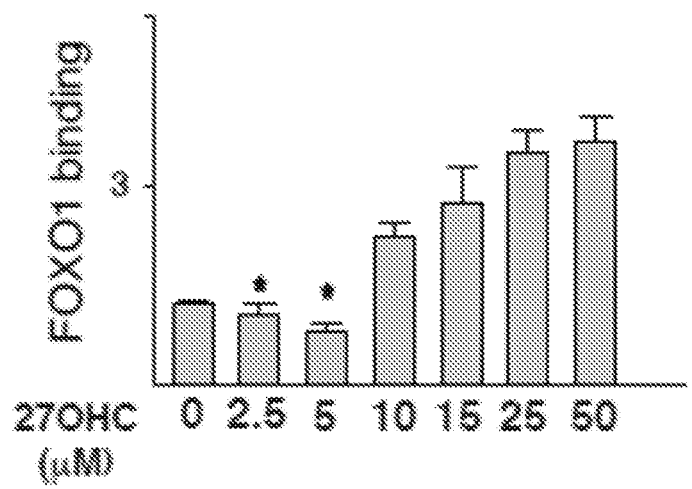
FIG. 4A-FIG. 4D. RTKN2 protein is necessary to generate a hormetic response to 27OHC. (A-C) Cytoprotective doses of 27OHC (2.5 and 5 µM) lead to decreased binding of FOXO1 to the RTKN2 promoter, as measured by ChIP assay (A), and to increased RTKN2 mRNA (B) and protein expression (C), (D) RTKN2 knockdown reverses cytoprotection in cells exposed to 5 µM 27OHC, as measured by expression profiles of activated caspase-3, activated caspase-7 and Bax/Bcl2 ratio.
Figure 4B:
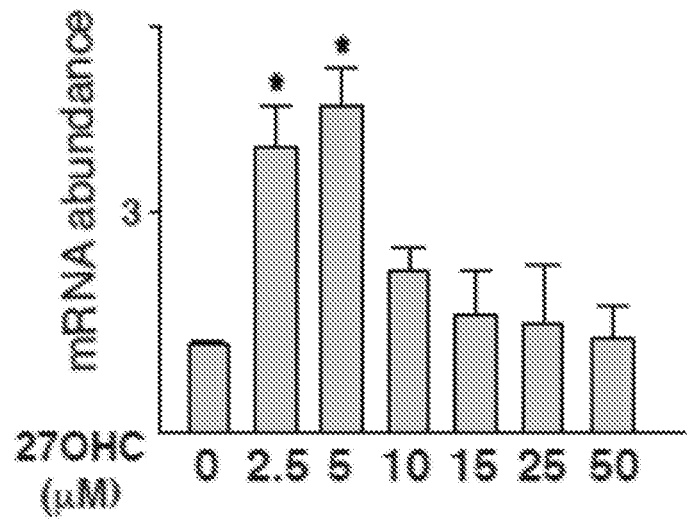
Figure 4C:
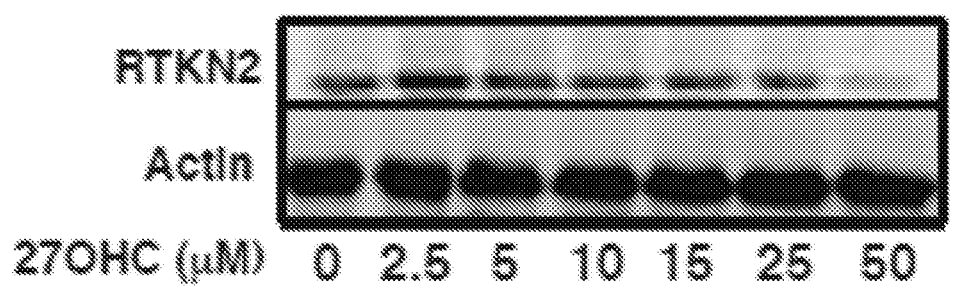

Next, we confirmed, in rat cortical neurons, that the binding of FOXO1 to the RTKN2 promoter in response to 27OHC follows a dose-dependent pattern such that FOXO1 binding decreased at cytoprotective 2.5 and 5 µM 27OHC doses while increasing at 15, 25, and 50 µM 27OHC (FIG. 4A), which correlated inversely not only with RTKN2 mRNA expression (FIG. 4B) but also with RTKN2 protein expression patterns (FIG. 4C). Thus, in response to cytoprotective doses of 27OHC, MAST4-mediated phosphorylation of FOXO1 controls FOXO1-mediated RTKN2 transcription.

Figure 4D:
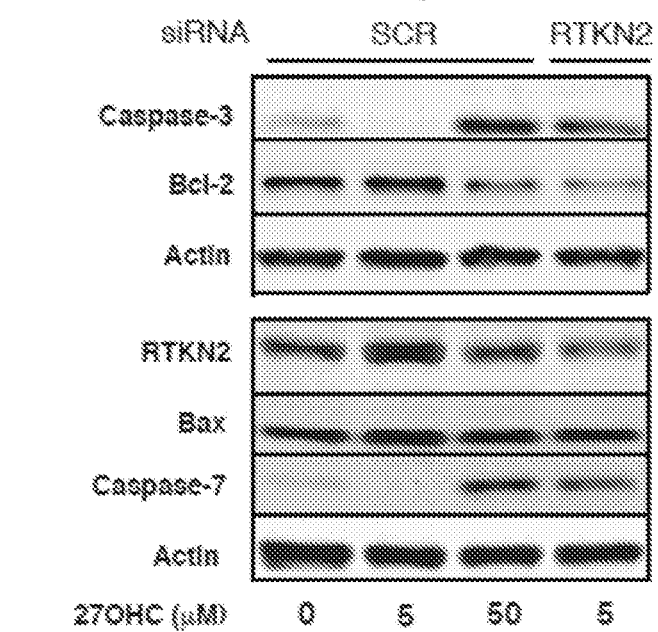

Next, to demonstrate that RTKN2 expression is required for the cytoprotective effect seen in response to 27OHC, we measured active caspases 3 and 7 as well as Bax and Bcl-2 following treatments with cytoprotective 5 µM or cytotoxic 50 µM 27OHC. Exposure to 50 µM 27OHC increased the active forms of both caspases, and decreased Bcl-2 (FIG. 4D). By comparison, exposure to 5 µM 27OHC resulted in a robust increase in Bcl-2 and RTKN2 and a decrease in active forms of both caspases, Crucially, knocking down RTKN2 reversed this pattern, demonstrating that expression of this oxysterol stress responder is necessary for the observed cytoprotective response to 27OHC, Taken together, these data validate the key elements of the proposed molecular model (FIG. 1I) that responds hermetically to 27OHC doses.

APP Governs RTKN2 Expression Through MAST4 and FOXO1 In Vivo

Figure 5A:
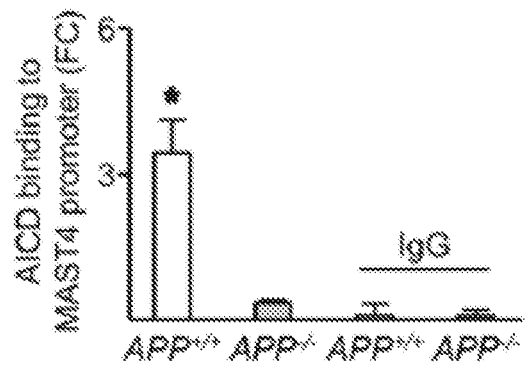
FIG. 5A-FIG. 5E. APP ablation decreased AICD/MAST4/FOXO1 signaling in vivo. ACID binding to the MAST4 promoter (A), MAST4 mRNA abundance (B). FOXO binding to the RTKN2 promoter (C), RTKN2 mRNA abundance (D), and immunoblotting of MAST4 and RTKN2 (upper panel) with quantification (lower panel) (F) in $APP^{+/+}$ or $APP^{-/-}$ mouse cortical samples. (A-E) N=3 independent experiments.
Figure 5B:
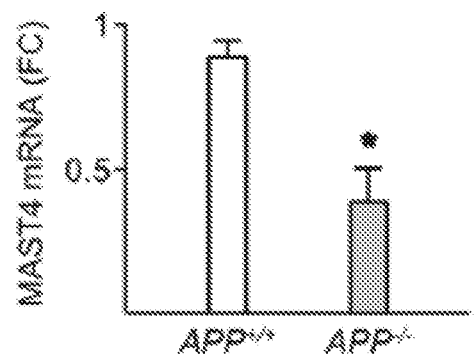
Figure 5C:
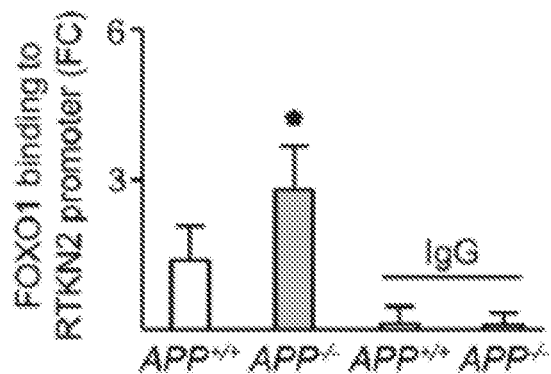
Figure 5D:
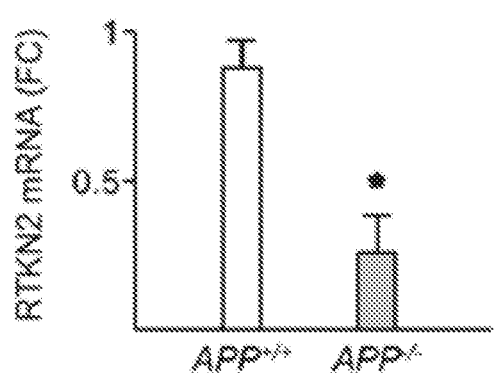
Figure 5E:
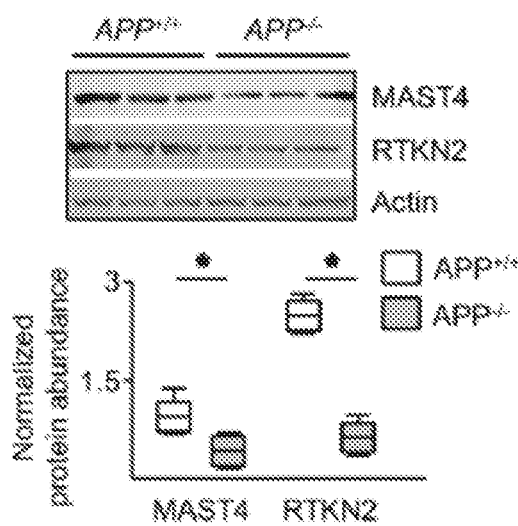

Our results thus far demonstrate that, in cultured cells, APP initiates a hormetic adaptive response to 27OHC, whose key elements are represented in FIG. 1I: AICD modulates an adaptive response to 27OHC such that, at lower levels (i,e., 5 µM in our cell models), 27OHC initiates a protective response involving MAST4-dependent FOXO1 regulation of the oxysterol stress-response protein RTKN2, whereas higher levels of 27OHC (i.e., 50 µM) fail to initiate that adaptive response. To determine if APP is important for the basal activation of the AICD-MAST4-FOXO1-RTKN2 pathway in viva, cerebral cortices from $APP^{+/+}$ mice and $APP^{-/-}$ littermates fed a normal diet, mimicking 5 µM 27OHC, were used. Higher AICD binding to the MAST4 promoter and MAST4 mRNA abundance was observed in $APP^{+/+}$ relative to $APP^{-/-}$ brains (FIG. 5A-B). Further, FOXO1 binding to the RTKN2 promoter was lower and RTKN2 mRNA was higher in $APP^{+/+}$ brains compared to $APP^{-/-}$ brains (FIG. 5C-D). Finally, both MAST4 and RTKN2 and protein abundance were higher in the $APP^{+/+}$ brains compared to $APP^{-/-}$ brains (FIG. 5E). These findings indicate that AICD-MAST4-FOXO1-RTKN2 signaling is intact in vivo.

Figure 6A:
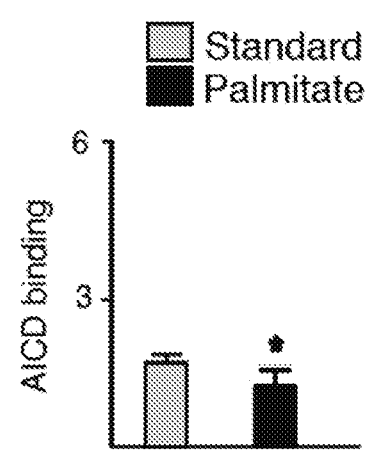
FIG. 6A-FIG. 6F. The AICD/MAST4/FOXO1 signaling pathway is altered in mice fed a high-fat diet. (A, B) ChIP shows that binding of AICD to the MAST4 promoter decreases in brains of mice fed a high-fat diet when compared to mice fed a control diet (A), which coincides with reduced MAST4 mRNA (B). (C, D) ChIP shows that binding of FOXO1 to the RTKN2 promoter increases in brains of mice fed high-fat when compared to mice fed a control diet (C), which coincides with a decrease in RTKN2 mRNA. (E, F) Western blot (E) and quantitation (F) of RTKN2 protein expression in brains of mice fed high-fat or control diets (F).
Figure 6B:
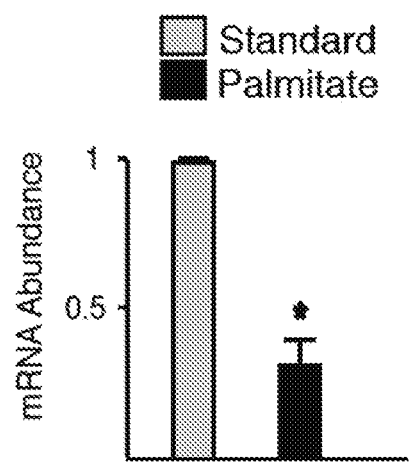
Figure 6C:
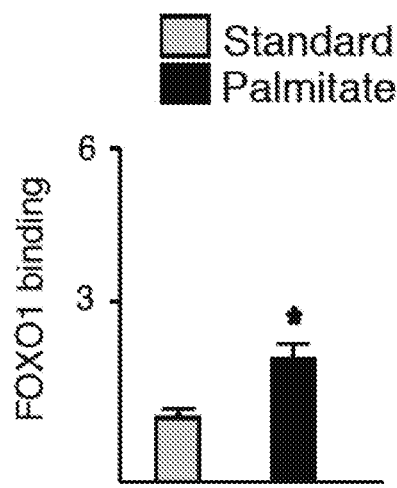
Figure 6D:
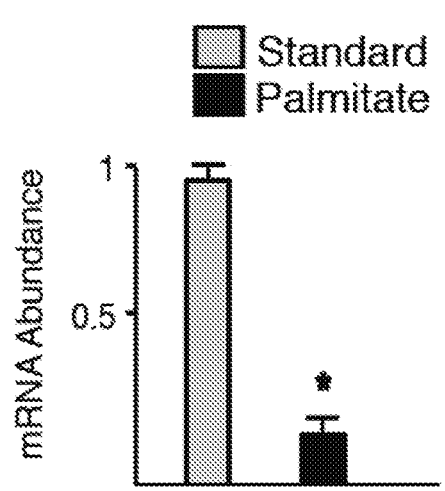
Figure 6E:
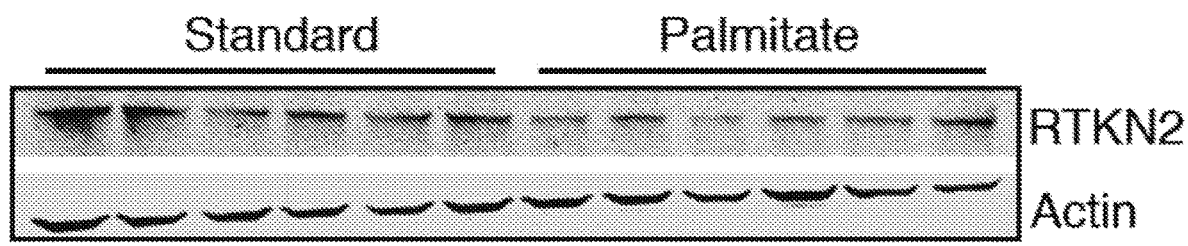
Figure 6F:
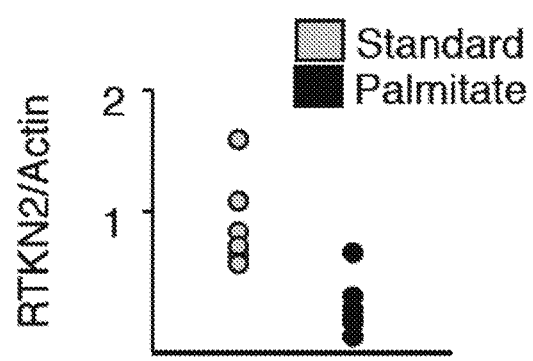

According to our model of neurodegeneration that places APP as the mediator of an adaptive response to cholesterol dysregulation (2, 8), a failed adaptive response would reflect a disease phenotype in the brain akin to what we observe at cytotoxic doses in vitro. To determine whether that is the case, we used an obesogenic mouse model of cognitive impairment. 6-week old mice were fed a palmitic acid-rich diet or a control diet for 16 weeks and the status of the AICD-MAST4-FOXO1-RTKN2 functional interactions determined. Palmitic acid is the most abundant fatty acid in typical obesogenic Western diets associated with AD pathology and higher risk of the disease (16-21). It leads to secondary 27OHC accumulation (22, 23); it causes CNS resistance to insulin and leptin (24, 25), which leads to obesity and the health risks associated with it, including AD (26, 27), and it causes cognitive and behavioral impairment (28, 29). Furthermore, FOXO1 is a shared mediator of both insulin and leptin (30, 31), and 27OHC attenuates leptin expression (32). Thus, we reasoned that the disease phenotype associated with this model of cognitive impairment could be accompanied by evidence of a failed AICD-driven adaptive response to dyslipidemia. As illustrated in FIG. 6, binding of AICD to the MAST4 promoter decreased in the high-fat diet group (FIG. 6A), which coincided with lower levels of MAST4 mRNA (FIG. 6C), whereas FOXO1 binding to the RTKN2 promoter increased (FIG. 6B), concomitantly with lower RTKN2 mRNA and protein levels (FIG. 6D-6F). Thus, as observed in cells exposed to high levels of 27OHC (e.g., as shown in FIGS. 1-4), loss of AICD-driven regulation of MAST4, FOXO1 and RTKN2 is also evident in the brains of mice fed an obesogenic palmitic acid-rich diet.

AICD-Driven Regulation of RTKN2 is Impaired in Late-Onset AD

Figure 7A:
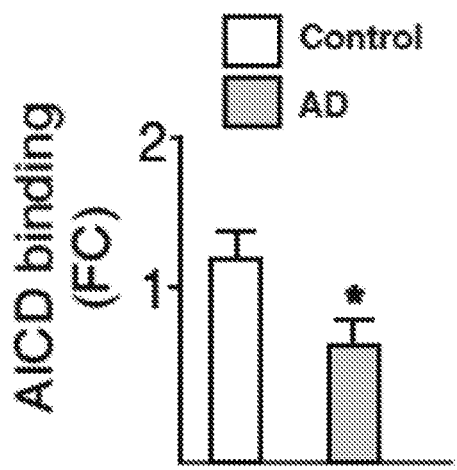
FIG. 7A-FIG. 7N. The AICD/MAST4/FOXO1 signaling pathway is altered in the temporal lobe of late onset AD but not in frontotemporal dementia (FTD). (A, B) ChIP shows that binding of AICD to the MAST4 promoter decreases in temporal lobe of late onset AD patients when compared to cognitively functional controls (A), concomitant with a decrease in MAST4 mRNA (B). (C, D) ChIP shows that binding of FOXO1 to the RTKN2 promoter increases in temporal lobe of late onset AD patients when compared to cognitively functional controls (C), concomitant with a decrease in RTKN2 mRNA (D). (E, F) Western blot (E) and quantitation (F) of RTKN2 levels in temporal lobe of AD patients and cognitively healthy controls. (G, H) Kinase assays demonstrate reduced MAST4 kinase activity in temporal lobe of late-onset AD patients relative to control samples. AICD binding to the MAST4 promoter (I), MAST4 mRNA abundance (J), FOXO1 binding to the RTKN2 promoter (K) and RTKN2 mRNA abundance (L) in the temporal lobe from AD and FTD patients. Immunoblotting (upper panels) and quantification (lower panels) of RTKN2 from temporal lobe samples from patients with AD (M), FTD (N), or normal cognitive function. Panels M and N contain the same three Normal samples loaded in each gel. ChIP and mRNA abundance are represented as fold change measurements (FC). (I-J) N=5 samples. (K-N) normal N=3 samples, AD N=11 samples, FTD N=9 samples. * P<0.05 significance is in comparison to normal samples.
Figure 7B:
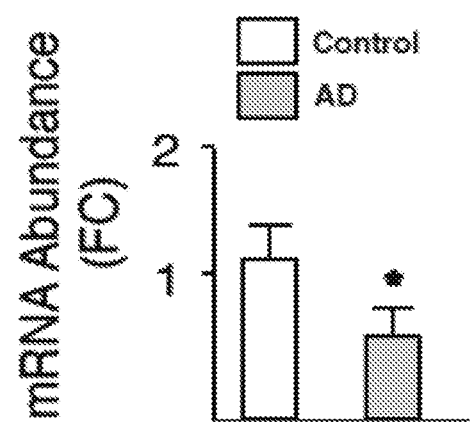
Figure 7C:
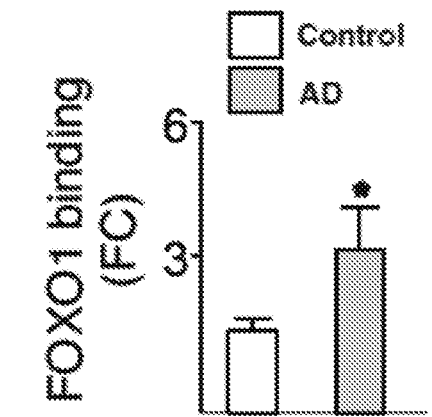
Figure 7D:
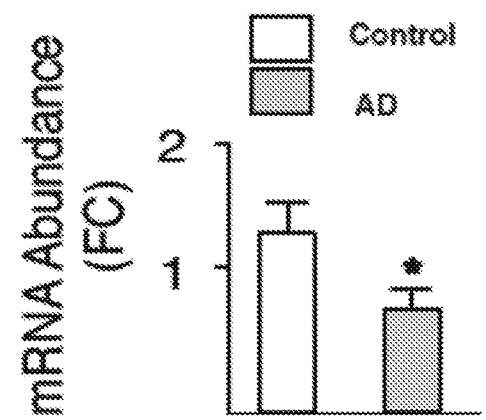
Figure 7E:
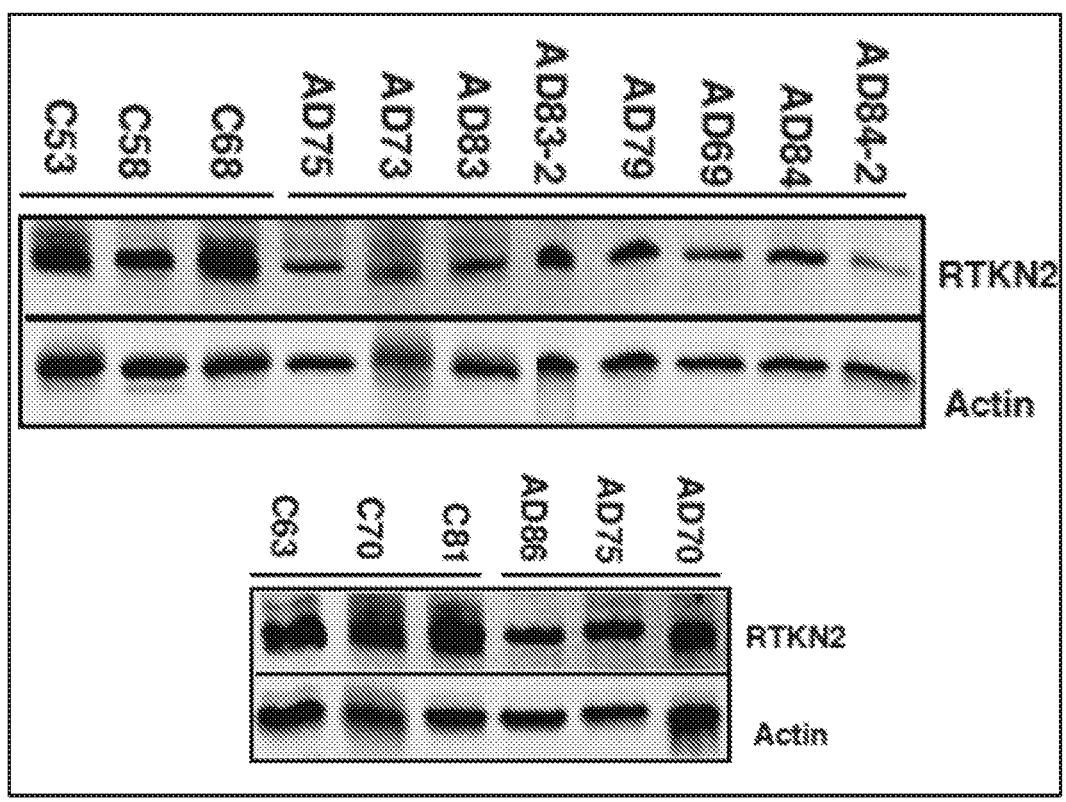
Figure 7F:
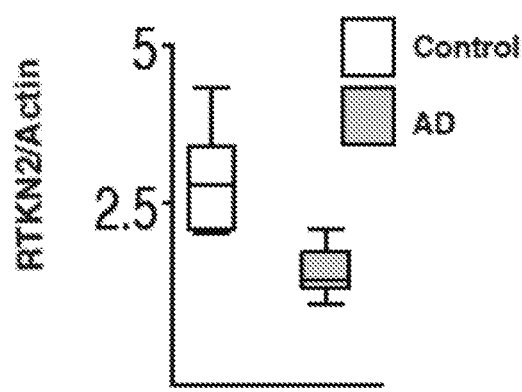
Figure 7G:
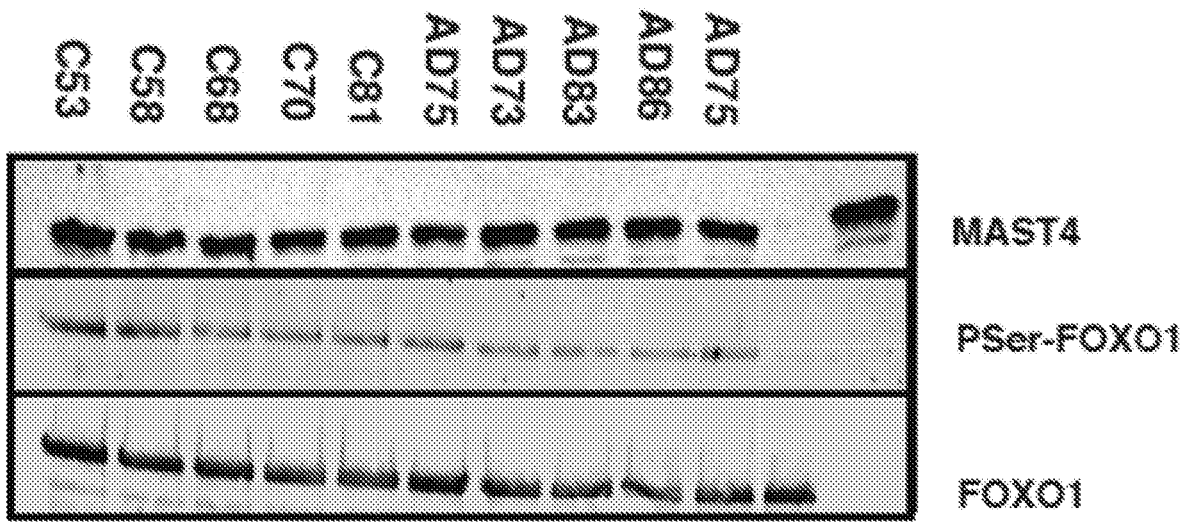
Figure 7H:
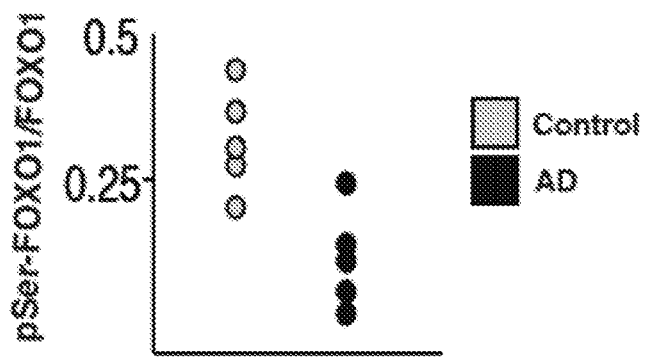
Figure 7I:
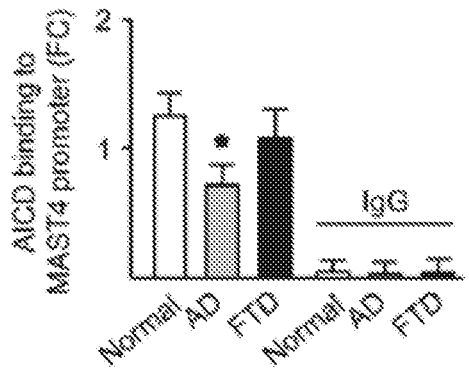
Figure 7J:
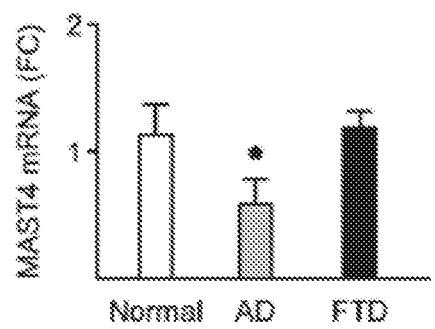
Figure 7K:
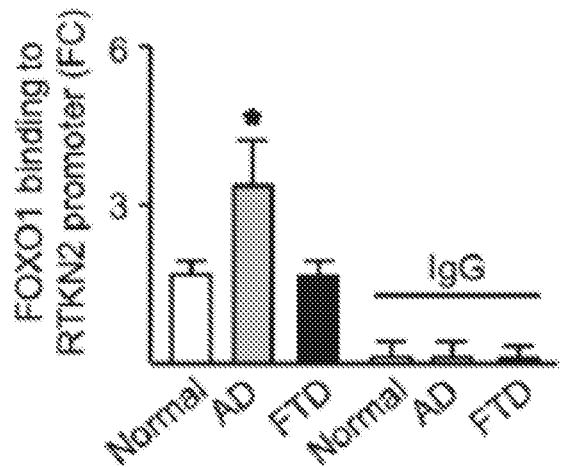
Figure 7L:
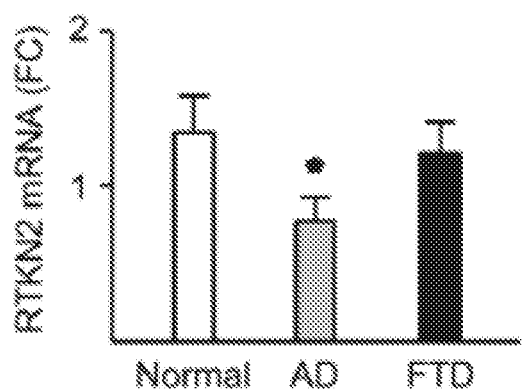
Figure 7M:
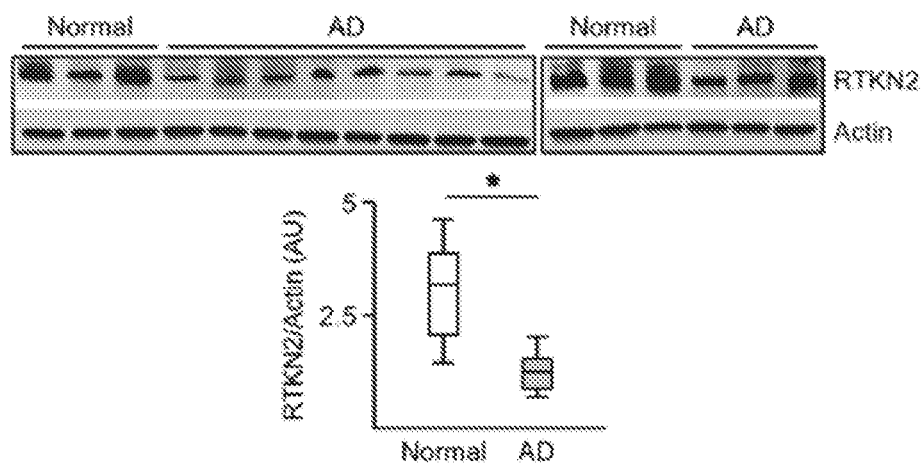
Figure 7N:
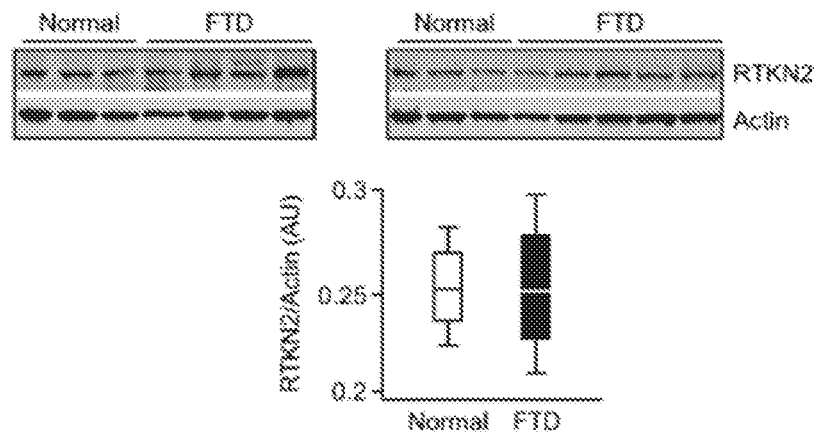

Our findings thus far show that in vitro exposure to cytotoxic levels of 27OHC as well as in vivo dyslipidemia associated with cognitive impairment and to 27OHC accumulation result in impaired functional interactions within the cytoprotective AICD-MAST4-FOXO1-RTKN2 pathway, ultimately leading to lower expression of the cell stress responder RTKN2. This is consistent with our model of neurodegeneration for late-onset AD, in which the transcriptional activity of APP is necessary to drive an adaptive response that supports appropriate brain homeostasis and cognitive function in response to dyslipidemia, including cholesterol dysregulation (2, 8). If that model were correct, we would expect an impaired AICD-MAST4-FOXO1-RTKN2 pathway in the late-onset AD brain. To test that notion, we measured AICD-MAST4 promoter and FOXO1-RTKN2 promoter interactions, as well as MAST4 and RTKN2 expression, in temporal lobe from autopsy samples from patients suffering from late-onset AD as well as cognitively healthy individuals and patients having frontotemporal dementia (FTD). We found decreased binding of AICD to the MAST4 promoter in the brains of late-onset AD patients when compared to cognitively healthy individuals and FTD brains (FIG. 7A and FIG. 7I), which was accompanied by lower MAST4 mRNA and protein levels for the AD patients (FIG. 7B and FIG. 7J). FOXO1 binding to the RTKN2 promoter was increased in AD patients as compared to control samples and FTD samples (FIG. 7C and FIG. 7K). RTKN2 mRNA and protein levels were decreased in samples from AD patients as compared to control samples or FTD samples (FIG. 7D, FIG. 7L, FIG. 7M, and FIG. 7N). Thus, the status of the AICD-driven molecular pathway in the late-onset AD brain is comparable to that observed in cultured cells exposed to cytotoxic doses of 27OHC and in the brain of mice fed a typical Western diet associated with cognitive impairment and 27OHC dysregulation in mice and with a higher risk of late-onset AD in humans. Finally, we conducted in vitro kinase assays with recombinant FOXO1 and immunoprecipitated MAST4 from lysates derived from control, FTD, or late-onset AD temporal lobe autopsy samples to test whether MAST4 kinase activity, as is the case in cells exposed to cytotoxic levels of 27OHC, decreases in the late-onset AD brain. As shown in FIGS. 7G and 7H, this was indeed the case. These results elucidate a novel APP regulated cytoprotective pathway in normal and FTD brains that is not active in the late-onset AD brains.

Discussion

We report here a novel signaling pathway in which the transcriptional activity of APP drives a hormetic response to 27OHC, an early marker of cholesterol dysregulation in the late-onset AD brain (9, 10). The molecular mechanism involves the regulation of MAST4 kinase and FOXO1 to optimize the expression of the oxysterol stress responder RTKN2 to counter 27OHC cytotoxicity. This adaptive response is absent in a dyslipidemia mouse model of cognitive decline and in the brain of human late-onset AD patients, both of which display aberrant 27OHC regulation, but it is not altered in the FTD brain, whose onset is not primarily linked to dyslipidemia or oxysterol dysregulation. In addition, a successful adaptive response requires a functional cholesterol-sensing domain in APP, also shown to bind to oxysterols (14, 33, 34).

The existence of an APP-driven hormetic adaptive response that is evident in the healthy brain but absent in late-onset AD is conceptually significant. Hormesis has been reported in the brain in response to a wide variety of stress stimuli, including oxidative stress, energy deprivation, glutamate, carbon monoxide, TNFα, and various phytochemicals (35, 36). It has been suggested that it could also exist as a protective mechanism in dementia against early pathogenic triggers (37, 38), and our findings here provide currently lacking mechanistic support for the existence of hormesis to neurodegenerative stressors relevant to life style risk factors associated with late-onset Alzheimer's disease.

Furthermore, the unveiling of APP as the driver of this hormetic response provides a new reference frame for understanding its function in disease etiology, as it defines it beyond its currently accepted role solely as the precursor of the amyloid peptide A13 within a primary pathogenic cascade, a view that lacks an evident pathophysiological context and does not fit the overall evidence (2, 5, 8). Ultimately, the finding that the adaptive response to 27OHC is deficient in the late-onset AD brain provides a rational basis for its optimization to inform the search for evidence-based therapy.

Materials and Methods

Bioinformatics and Data Mining

Entrosolve (Entrosolve.com) was recruited to mine all large datasets, conduct consensus sequence mapping, and identify signaling pathways.

Cell Isolation and Culture

Rat cortical neurons were dissociated using a papain dissociation kit following manufacturer's instructions (Worthington, N.J; Cat #LK003150). Neurons were cultured in neurobasal medium with B27 supplement with 2 mM glutamine, 50 U/mL penicillin and 50 μg/mL. SH-SY5Y and B103 cells were cultured in DMEM (Sigma Cat #D6429-500M) supplemented with 5% fetal bovine serum. SH-SY5Y cells were differentiated with the addition of 10 μM retinoic acid for 7 days prior to experimentation.

Transfection

Transfections were conducted using Lippofectamine LTX (Thermofisher; cat #A12621) according to the manufacturer's instructions.

Human Brains

Postmortem tissue was obtained from the Easton Alzheimer's Disease Research Center Brain Bank at the University of California, Los Angeles. Diagnoses were established using accepted clinical and histopathologic criteria.

All patients and/or their legal guardians gave their informed consent to participate in research protocols prior to tissue donation. All methods and protocols, including those necessary to ensure the privacy rights of human subjects, were carried out in accordance with relevant institutional regulations and were approved by Institutional Review Board of Loma Linda University Medical Center approval #54174).

Animal Studies

All animal procedures were carried out in accordance with the U.S. Public Health Service Policy on the Humane Care and Use of Laboratory Animals and were approved by the Institutional Animal Care and Use Committee at the University of North Dakota (Protocol 1506-3c). All animal experiments comply with the National Institutes of Health guide for the care and use of Laboratory animals (NIH Publications No. 8023, revised 1978). The mice were housed in individually ventilated cages at an ambient room temperature (23-25° C.) and ambient relative humidity ranging between 50 and 70%. The mice were maintained on 12:12 h light: dark cycle. Male C57BL/6J mice (6-week-old) were fed a normal or palmitate-enriched diet for 16 weeks (n=6 per group). The normal diet contains 0.8% palmitate and 2.2% linoleic acid (NIH-07 open Formula Mouse, TD. 8+5172; Herian Teklad). The palmitate-enriched diet is formulated by adding 30 g/kg palm oil (3%) to NIH-07 mice diet to increase the palmitic acid from 0,8 to 2.2% by weight and lowering linoleic acid from 2.2% to 0.8% (TD.110616, Harlan Teklad). Control and palmitate diets are isocaloric, the key difference residing in the palmitate levels.

Microarray Transcriptional Profiling

Mice used in this study to generate microarray transcriptomes have been described in detail (Nunes et al., *Neurobiol Dis.*, 2011, 42:349-59). Samples were flash-frozen in liquid nitrogen, and frozen samples sent to Genus Biosystems (Northbrook, Il) for Micro Array transcriptional profiling.

RNA purification

RNA was purified using TRIzol LS reagent according to the manufacturer's instructions (Thermofisher cat #10296010).

Chromatin Immunoprecipitation Assays

Chromatin Immunoprecipitation (ChIP) assays were conducted according to standard protocols published by ABcam. Following treatments, cells were incubated with formaldehyde at a final concentration of 0.75% for 10 minutes followed by glycine at a final concentration of 125 mM for an additional 5 minutes. Cells were then washed two times with Phosphate Buffered Saline (PBS) and lysed in FA lysis buffer (50 mM HEPES-KOH pH 7.5, 140 mM NaCl, 1 mM EDTA, 1% Triton X-100, 0.1% Sodium Deoxycholate, 0.1% SDS, protease inhibitors). Resulting cell lysates were sonicated to fragment DNA, spun down, and incubated with antibody conjugated protein A sepharose beads (ThermoFisher cat #101041) overnight with gentile agitation. Following incubation, beads were pelleted, washed three times with FA lysis buffer, and DNA was eluted with elution buffer (1% SDS, 100 mM NaHCO₃). Resulting DNA fragments were further purified with a DNA purification kit (Clontech cat #740609.250) prior to qPCR analysis. Antibodies used were anti-APP C-terminus (Sigma #A8717); anti-FOXO1 (Abeam #39670). Primer sequences are listed in Table 1.

TABLE 1

Primer sequences

| | Forward Sequence | Reverse Sequence |
|---|---|---|
| Human mRNA Primers | | |
| RTKN2 | CCAGAGGAAATTGAAGC TAAAGTG | TGTCCAGGAACAGGATTGATG |
| MAST4 | GTGGAATTGCTTGGTCA AACG | ACTGATGCAACTTCTCCTGG |
| β-Actin | CATGTACGTTGCATCCA GGC | CTCCTTAATGTCACGCACGAT |
| Mouse mRNA Primers | | |
| RTKN2 | CTTGGAAAATGCTGGAG ACTG | GAGATCAAAGAAATGTTGCCGG |
| MAST4 | AAAGTCACAAAGTCCCT CTCG | ACCTTATTCCCACTCTTCAGC |
| β-Actin | AGGCCGGTGCTGAGTAT GTC | TGCCTGCTTCACCACCTTCT |
| Rat mRNA Primers | | |
| RTKN2 | GAAAGCGGATATGTGAG AGGG | CACTCTAGCCGAATGTACTGG |
| MAST4 | AGTCCATAAAGCGTCCA AGC | TTCTTGTAACTCCCATCCTGC |
| β-Actin | GGGAAATCGTGCGTGAC ATT | GCGGCAGTGGCCATCTC |
| Human Promoter Primers | | |
| RTKN2 | GATATCGACCTTCTGTA AGAGCC | AGTTCCCAGAAAGTGAGAAGTAC |
| MAST4 | CACAACTCACCTCTGAT TCTCC | ACCCTACTCCTGCCTCTTAC |
| β-Actin | CGACCAGTGTTTGCCTT TTATG | ATGGTGAGCTGCGAGAATAG |
| Mouse Promoter Primers | | |
| RTKN2 | CATCCTCAGCTACCACT CTTTAAG | AGAACCAGCCATCAACACG |
| MAST4 | CTCCTGGGTACATCTCC TTTTG | CAAAAGGAGATGTACCCAGGAG |
| GAPDH | CCCTGTTCTCCCATTTT ACTCG | GCTTATCCAGTCCTAGCTCAAG |
| Rat Promoter Primers | | |
| RTKN2 | ATTTTCACCTCTTACC GGCTC | AGGACACCCAGAATACACAAC |
| MAST4 | TCTGGGTATGCTAGGC TTAGG | AAGGACTATCTGATTGGCTGAC |
| β-Actin | GAGTGGTCAAGATCCC TGAAG | AGAGGATGAAGAGTTTGGCG | qPCR mRNA was purified with TRIzol reagent, converted to cDNA with reverse transcriptase according to the manufacturer's instructions and quantified with iTaq Universal SYBR Green Supermix (Bio-Rad cat #1725120). Results were determined using the delta-delta cycle threshold (ct) method. Primer sequences are listed in Table 1.

Immunoblotting

Immunoblotting was conducted as previously described with the following antibodies: APP (Sigma #A8717; Millipore #22C11); MAST4 (GeneTex #GTX87899); FOXO1 (Cell Signaling Technology #2880); RTKN2 (Proteintech

17458-1-AP); caspase-3 (Cell Signaling Technology #9662); caspase-7 (Cell Signaling Technology #9492); actin (Sigma #A5316) (7).

Immunoprecipitation

Immunoprecipitations were conducted as outlined by ABcam under non-denaturing conditions.

MAST4 In Vitro Kinase Assay

Kinase activity was measured at 37° C. for 30 minutes in 50 µl kinase buffer (50 mM Tris, pH 7.4, 10 mM MgCl2) supplemented with 50 µM ATP and human recombinant FOXO1 (1 µg; Origene #TP300477). Kinase reactions were run on 4-20% Tris-Glycine polyacrylamide gels (Thermofisher) and byproducts identified with anti phospho-Serine/Threonine antibody (Abcam ab17464).

LDH Assay

LDH assays were conducted with a LDH assay kit following manufacturer's instructions cattt 88954).

Live Dead Cell Assay

Live dead cell assays were conducted with live dead cell assay kit according to the manufacturer's instructions (Thermofisher #L3224).

Lipid Raft Fractionation

Lipid rafts were isolated using a detergent-free method. Specifically, cells were grown to 80% confluence in 10 cm dishes, washed twice with ice cold PBS before being lysed with 2 ml of 100 mM Na2CO3, pH 11.0 plus Halt™ protease and phosphatase inhibitor cocktail (Thermofisher cat #78443). The cell suspension was homogenised with 8 strokes of a Dounce homogeniser and then sonicated using continuous sonication with a Vibra Cell (Sonics and Materials, USA) on power setting 1 (3×20 s). The homogenate was then adjusted to 45% sucrose by mixing with 2 ml of 90% (w/v) sucrose solution in MBS buffer and then added to a 12 ml Beckman ultrclear centrifuge tube. 4 ml of 35% (w/v) sucrose was carefully layered on top, followed by 4 ml of 5% (w/v) sucrose solution. 90% (w/v) sucrose solution was prepared in MBS buffer (25 mM Mes, 150 mM NaCl, pH 6.5). Both the 35% and 5% sucrose solutions were prepared in MBS buffer plus 250 mM $Na_2CO_3$. The samples were then centrifuged at 175000 g (39000 rpm using a Beckman SW41 rotor) for 18 h at 4° C. 1 ml fractions were taken from the top of the tube and stored at −20° C.

Statistical Analysis

Data are means±SEM of at least three independent experiments. Tests used for nonparametric data included Kruskal-Wallis test with Tukey's post hoc test and Mann-Whitney U test. Parametric data were analyzed using analysis of variance (ANOVA) with post hoc Bonferroni. Unless otherwise indicated, P values<0.05 are considered statistically significant.

REFERENCES

1. J. Hardy, A. D. Mayer, The amyloid cascade hypothesis has misled the pharmaceutical industry. Biochem Soc Trans 39, 920-923 (2011).
2. M. A. Castello, J. D. Jeppson, S. Soriano, Moving beyond anti-amyloid therapy for the prevention and treatment of Alzheimer's disease. BMC Neural 14, 169 (2014).
3. N. N. Nalivaeva, A. J. Turner, The amyloid precursor protein: a biochemical enigma in brain development, function and disease. FEBS Lett 587, 2046-2054 (2013).
4. R. J. Castellani et al., Reexamining Alzheimer's disease: evidence for a protective role for amyloid-beta protein precursor and amyloid-beta. J Alzheimers Dis 18, 447-452 (2009).
5. K. Herrup, The case for rejecting the amyloid cascade hypothesis. Nat Neurasci 18, 794-799 (2015).
6. J. A. Blair et al., Accumulation of intraneuronal amyloid-beta is common in normal brain. Curr Alzheimer Res 11, 317-324 (2014).
7. D. K. Kumar et al., Amyloid-beta peptide protects against microbial infection in mouse and worm models of Alzheimer's disease. Sci Transl Med 8, 340ra372 (2016).
8. M. A. Castello, S. Soriano, Rational heterodoxy: cholesterol reformation of the amyloid doctrine. Ageing Res Rev 12, 282-288 (2013).
9. G. Marwarha, B. Dasari, J. R. Prasanthi, J. Schommer, O. Ghribi, Leptin reduces the accumulation of Abeta and phosphorylated tau induced by 27-hydroxycholesterol in rabbit organotypic slices. J. Alzheimers Dis 19, 1007-1019 (2010).
10. J. R. Prasanthi, T. Larson, J. Schommer, O. Ghribi, Silencing GADD153/CHOP gene expression protects against Alzheimer's disease-like pathology induced by 27-hydroxycholesterol in rabbit hippocampus. PLoS One 6, e26420 (2011).
11. M. P. Mattson, Hormesis and disease resistance: activation of cellular stress response pathways. Hum Exp Toxicol 27, 155-162 (2008).
12. P. Garland, S. Quraishe, P. French, V. O'Connor, Expression of the MAST family of serine/threonine kinases. Brain Res 1195, 12-19 (2008).
13. L. Sun et at., [Identification of a novel human MAST4 gene, a new member of the microtubule associated serine-threonine kinase family]. Mol Biol (Mosk) 40, 808-815 (2006).
14. P. J. Barrett et al., The amyloid precursor protein has a flexible transrnembrane domain and binds cholesterol. Science 336, 1168-1171 (2012).
15. J. E. Walker, M. Saraste, M. J. Runswick, N. J. Gay, Distantly related sequences in the alpha- and beta-subunits of ATP synthase, myosin, kinases and other ATP-requiring enzymes and a common nucleotide binding fold. EMBO J 1, 945-951 (1982).
16. G. L. Bowman, J. A. Kaye, J. F. Quinn, Dyslipidemia and blood-brain barrier integrity in Alzheimer's disease. Curr Gerontal Geriatr Res 2012, 184042 (2012).
17. M. W. Warren, L. S. Hynan, M. F. Weiner, Lipids and adipokines as risk factors for Alzheimer's disease. J Alzheimers Dis 29, 151-157 (2012).
18. C. Reitz, Dyslipidemia and the risk of Alzheimer's disease. Curr Atherascl Rep 15, 307 (2013).
19. S. Patil, C. Chan, Palmitic and stearic fatty acids induce Alzheimer-like hyperphosphorylation of tau in primary rat cortical neurons. Neurasci Lett 384, 288-293 (2005).
20. S. Patil, D. Balu, J. Melrose, C. Chan, Brain region-specificity of palrnitic acid-induced abnormalities associated with Alzheimer's disease. BMC Res Notes 1, 20 (2008).
21. T. Fraser, H. Tayler, S. Love, Fatty acid composition of frontal, temporal and parietal neocortex in the normal human brain and in Alzheimer's disease. Neurochem Res 35, 503-513 (2010).
22. M. Umetani et al., 27-Hydroxycholesterol is an endogenous SERM that inhibits the cardiovascular effects of estrogen. Nat Med 13, 1185-1192 (2007).
23. J. S. Wooten et al., The Influence of an Obesogenic Diet on Oxysterol Metabolism in C57BL/6J Mice. Cholesterol 2014, 843468 (2014).

24. K. A. Posey et al., Hypothalamic proinflammatory lipid accumulation, inflammation, and insulin resistance in rats fed a high-fat diet. *Am J Physiol Endocrinol Metab* 296, E1003-1012 (2009).
25. S. C. Benoit et al., Palmitic acid mediates hypothalamic insulin resistance by altering PKC-theta subcellular localization in rodents. *J Clin Invest* 119, 2577-2589 (2009).
26. G. H. Doherty, Obesity and the ageing brain: could leptin play a role in neurodegeneration? *Curr Gerontol Geriatr Res* 2011, 708154 (2011).
27. E. B. Lee, Obesity, leptin, and Alzheimer's disease. *Ann N Y Acad Sci* 1243, 15-29 (2011).
28. M. L. Moon et al., The saturated fatty acid, paimitic acid, induces anxiety-like behavior in mice. *Metabolism* 63, 1131-1140 (2014).
29. M. A. Beydoun, J. S. Kaufman, J. A. Satia, W. Rosamond, A. R. Folsom, Plasma n-3 fatty acids and the risk of cognitive decline in older adults: the Atherosclerosis Risk in Communities Study. *Am J Clin Nutr* 85, 1103-1111 (2007).
30. H. Huang et al., Rho-kinase regulates energy balance by targeting hypothalamic leptin receptor signaling. *Nat Neurosci* 15, 1391-1398 (2012).
31. M. S. Kim et al., Role of hypothalamic Foxo1 in the regulation of food intake and energy homeostasis. *Nat Neurosci* 9, 901-906 (2006).
32. G. Marwarha, B. Dasari, O. Ghribi, Endoplasmic reticulum stress-induced CHOP activation mediates the downregulation of leptin in human neuroblastoma SH-SY5Y cells treated with the oxysterol 27-hydroxycholesterol. *Cell Signal* 24, 484-492 (2012).
33. L. Lecanu et at., Identification of naturally occurring spirostenols preventing beta-amyloid-induced neurotoxicity. *Steroids* 69, 1-16 (2004).
34. Z. X. Yao, R. C. Brown, G. Teper, J. Greeson, V. Papadopoulos, 22R-Hydroxycholesterol protects neuronal cells from beta-arnyloid-induced cytotoxicity by binding to beta-amyloid peptide. *J Neurochem* 83, 1110-1119 (2002).
35. V. Calabrese et at., Major pathogenic mechanisms in vascular dementia: Roles of cellular stress response and horrnesis in neuroprotection. *J Neurosci Res*, (2016).
36. S. J. Texel, M. P. Mattson, Impaired adaptive cellular responses to oxidative stress and the pathogenesis of Alzheimer's disease. *Antioxid Redox Signal* 14, 1519-1534 (2011).
37. J. Smith Sonneborn, Alternative strategy for Alzheimer's disease: stress response triggers. *Int J Alzheimers Dis* 2012, 684283 (2012).
38. J. G. Geisier, K. Marosi, J. Halpern, M. P. Mattson, DNP, mitochondrial uncoupling, and neuroprotection: A little dab'll do ya. *Alzheimers Dement*, (2016).

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

---

What is claimed is:

1. A method of treating a subject by delaying or reversing the progression of Alzheimer's disease, the method comprising:
   obtaining a sample containing a brain tissue of the subject;
   measuring in the sample from the subject a level of expression of microtubule-associated Ser/Thr kinase 4 (MAST4) polynucleotide or protein;
   comparing the level of expression of MAST4 of the sample with a reference MAST4 value;
   assessing a risk of progression to Alzheimer's disease for the subject with a decreased level of expression of MAST4 as compared to the reference MAST4 value;
   administering a lipid-lowering or cholesterol-lowering medication to the subject; and
   treating the subject.

2. The method of claim 1, wherein the method further comprises: measuring in the sample from the subject (i) a level of expression of a rhotekin 2 (RTKN2) polynucleotide or protein, and (ii) the level of expression of a MAST4 polynucleotide or protein; and determining that the sample from the subject has (i) decreased expression of RTKN2, and (ii) decreased expression of MAST4, as compared to the reference MAST4 value and a reference RTKN2 value.

3. The method of claim 2, wherein the method further comprises: measuring in the sample from the subject (i) the level of expression of a RTKN2 polynucleotide or protein, (ii) the level of expression of a MAST4 polynucleotide or protein, (iii) a level of binding of forkhead box O1 (FOXO1) to the RTKN2 promoter; and (iv) a level of binding of amyloid precursor protein (APP), or a fragment thereof comprising the APP intracellular domain, to the MAST4 promoter; and determining that the sample from the subject has (i) decreased expression of RTKN2, (ii) decreased expression of MAST4, (iii) increased binding of FOXO1 to the RTKN2 promoter, and (iv) decreased binding of APP or the fragment thereof to the MAST4 promoter in the sample from the subject, as compared to the reference MAST4 value, the reference RTKN2 value, a reference value of binding of FOXO1 to the RTKN2 promoter, and a reference value of binding of APP or the fragment thereof to the MAST4 promoter.

4. The method of claim 3, wherein the method further comprises:

measuring in the sample from the subject the level of phosphorylation of FOXO1 protein; and determining that the sample from the subject has decreased phosphorylation of FOXO1 in the sample from the subject, as compared to the reference value.

5. The method of claim 1, wherein the reference MAST4 value is determined by assessing a level of the MAST4 polynucleotide or protein in one or more samples containing brain tissue from one or more subjects with normal cognitive function.

6. The method of claim 1, wherein the reference MAST4 value is determined by assessing a level of the MAST4 polynucleotide or protein in one or more samples containing brain tissue from one or more subjects with mild cognitive impairment.

7. The method of claim 2, wherein the reference RTKN2 value is determined by assessing a level of the RTKN2 polynucleotide or protein in one or more samples containing or brain tissue from one or more subjects with normal cognitive function.

8. The method of claim 2, wherein the reference RTKN2 value is determined by assessing a level of the RTKN2 polynucleotide or protein in one or more samples containing brain tissue from one or more subjects with mild cognitive impairment.

\* \* \* \* \*

SEQUENCE LISTING

```
<160> NUMBER OF SEQ ID NOS: 41

<210> SEQ ID NO 1
<211> LENGTH: 59
<212> TYPE: PRT
<213> ORGANISM: Homo sapiens

<400> SEQUENCE: 1

Ile Ala Thr Val Ile Val Ile Thr Leu Val Met Leu Lys Lys Lys Gln
1               5                   10                  15

Tyr Thr Ser Ile His His Gly Val Val Glu Val Asp Ala Ala Val Thr
            20                  25                  30

Pro Glu Glu Arg His Leu Ser Lys Met Gln Gln Asn Gly Tyr Glu Asn
        35                  40                  45

Pro Thr Tyr Lys Phe Phe Glu Gln Met Gln Asn
    50                  55

<210> SEQ ID NO 2
<211> LENGTH: 57
<212> TYPE: PRT
<213> ORGANISM: Homo sapiens

<400> SEQUENCE: 2

Thr Val Ile Val Ile Thr Leu Val Met Leu Lys Lys Lys Gln Tyr Thr
1               5                   10                  15
```

Ser Ile His His Gly Val Val Glu Val Asp Ala Ala Val Thr Pro Glu
            20                  25                  30

Glu Arg His Leu Ser Lys Met Gln Gln Asn Gly Tyr Glu Asn Pro Thr
        35                  40                  45

Tyr Lys Phe Phe Glu Gln Met Gln Asn
    50                  55

<210> SEQ ID NO 3
<211> LENGTH: 50
<212> TYPE: PRT
<213> ORGANISM: Homo sapiens

<400> SEQUENCE: 3

Val Met Leu Lys Lys Lys Gln Tyr Thr Ser Ile His His Gly Val Val
1               5                   10                  15

Glu Val Asp Ala Ala Val Thr Pro Glu Glu Arg His Leu Ser Lys Met
            20                  25                  30

Gln Gln Asn Gly Tyr Glu Asn Pro Thr Tyr Lys Phe Phe Glu Gln Met
        35                  40                  45

Gln Asn
    50

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccagaggaaa ttgaagctaa agtg                                          24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtccaggaa caggattgat g                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtggaattgc ttggtcaaac g                                             21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
actgatgcaa cttctcctgg                                                    20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catgtacgtt gctatccagg c                                                  21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctccttaatg tcacgcacga t                                                  21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cttggaaaat gctggagact g                                                  21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagatcaaag aaatgttgcc gg                                                 22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaagtcacaa agtccctctc g                                                  21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
accttattcc cactcttcag c                                          21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aggccggtgc tgagtatgtc                                            20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgcctgcttc accaccttct                                            20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaaagcggat atgtgagagg g                                          21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cactctagcc gaatgtactg g                                          21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agtccataaa gcgtccaagc                                            20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttcttgtaac tcccatcctg c                                          21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gggaaatcgt gcgtgacatt                                               20

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
gcggcagtgg ccatctc                                                  17

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gatatcgacc ttctgtaaga gcc                                           23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
agttcccaga aagtgagaag tac                                           23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
cacaactcac ctctgattct cc                                            22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
accctactcc tgcctcttac                                               20

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgaccagtgt ttgccttttta tg                                            22

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atggtgagct gcgagaatag                                                20

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
catcctcagc taccactctt taag                                           24

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agaaccagcc atcaacacg                                                 19

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctcctgggta catctccttt tg                                             22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caaaaggaga tgtacccagg ag                                             22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
ccctgttctc ccatttttact cg                                              22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gcttatccag tcctagctca ag                                               22

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
attttcacct cttaccggct c                                                21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
aggacaccca gaatacacaa c                                                21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
tctgggtatg ctaggcttag g                                                21

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
aaggactatc tgattggctg ac                                               22

<210> SEQ ID NO 38

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gagtggtcaa gatccctgaa g                                             21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agaggatgaa gagtttggcg                                               20

<210> SEQ ID NO 40
<211> LENGTH: 8
<212> TYPE: DNA
<213> ORGANISM: Unknown
<220> FEATURE:
<223> OTHER INFORMATION: Description of Unknown:
      FOXO1 consensus sequence

<400> SEQUENCE: 40 ttrtttkk                                                            8

<210> SEQ ID NO 41
<211> LENGTH: 5
<212> TYPE: PRT
<213> ORGANISM: Unknown
<220> FEATURE:
<223> OTHER INFORMATION: Description of Unknown:
      MAST4 sequence

<400> SEQUENCE: 41

Val Leu Ala Leu Glu
1               5
```